(12) United States Patent
Lanza et al.

(10) Patent No.: US 7,179,449 B2
(45) Date of Patent: Feb. 20, 2007

(54) ENHANCED ULTRASOUND DETECTION WITH TEMPERATURE-DEPENDENT CONTRAST AGENTS

(75) Inventors: Gregory M. Lanza, St. Louis, MO (US); Samuel A. Wickline, St. Louis, MO (US); Christopher S. Hall, Houston, TX (US)

(73) Assignee: Barnes-Jewish Hospital, St. Louis, MO (US)

( * ) Notice: Subject to any disclaimer, the term of this patent is extended or adjusted under 35 U.S.C. 154(b) by 421 days.

(21) Appl. No.: 09/774,278

(22) Filed: Jan. 30, 2001

(65) Prior Publication Data

US 2002/0102216 A1 Aug. 1, 2002

(51) Int. Cl.
*A61B 5/055* (2006.01)
*A61B 8/00* (2006.01)
*A61K 9/127* (2006.01)

(52) U.S. Cl. .................. 424/9.321; 424/9.5; 424/9.51; 424/9.52; 424/450; 514/937; 514/938

(58) Field of Classification Search ............. 424/9.321, 424/9.5, 9.51, 9.52, 450; 514/937, 938
See application file for complete search history.

(56) References Cited

U.S. PATENT DOCUMENTS

| | | | |
|---|---|---|---|
| 4,863,713 A | 9/1989 | Goodwin et al. | |
| 5,149,319 A * | 9/1992 | Unger .......................... | 604/22 |
| 5,171,737 A | 12/1992 | Weiner et al. | |
| 5,242,681 A | 9/1993 | Elgavish et al. | |
| 5,401,634 A | 3/1995 | Milbrath | |
| 5,512,294 A | 4/1996 | Li et al. | |
| 5,527,528 A | 6/1996 | Allen et al. | |
| 5,536,489 A | 7/1996 | Lohrmann et al. | |
| 5,542,935 A | 8/1996 | Unger et al. | |
| 5,571,498 A | 11/1996 | Cacheris et al. | |
| 5,585,112 A | 12/1996 | Unger et al. | |
| 5,612,057 A | 3/1997 | Lanza et al. .................. | 424/450 |
| 5,616,690 A | 4/1997 | Axworthy et al. | |
| 5,733,526 A * | 3/1998 | Trevino et al. ............. | 424/9.52 |
| 5,840,023 A | 11/1998 | Oraevsky et al. ............ | 600/407 |
| 5,977,538 A | 11/1999 | Unger et al. .............. | 250/227.2 |
| 5,989,520 A | 11/1999 | Lanza et al. ................ | 424/9.32 |
| 6,123,923 A | 9/2000 | Unger et al. | |
| 6,159,445 A | 12/2000 | Klaveness et al. ........... | 424/9.6 |
| 6,375,931 B2 * | 4/2002 | .O slashed.stensen et al. ... | 424/9.52 |

OTHER PUBLICATIONS

Stensh, Dictionary of Biochemistry and Molecular Biology, 2nd ed, p. 152, 1989.*
Urdal, D.L., et al., "Tumor-associated Ganglio-N-triosylceramide," Journal of Biological Chemistry, Apr. 21, 1980, pp. 10509-10516, vol. 225, No. 21.
Narayana, et al., Temperature Variation of Ultrasonic Velocity in Some Low Velocity Fluorocarbon Liquids, Acoustics Letters, 1986, pp. 137-143, vol. 9.

(Continued)

*Primary Examiner*—Shengjun Wang
(74) *Attorney, Agent, or Firm*—Morrison & Foerster LLP

(57) ABSTRACT

Methods and devices for enhanced ultrasound detection based upon changing temperature and ultrasound reflectivity of a temperature-dependent contrast agent bound to an ultrasound target are disclosed. The methods and devices can be used for enhanced imaging alone or in conjunction with drug delivery, with therapeutic approaches such as hyperthermia or cryotherapy or with other imaging modalities.

22 Claims, 7 Drawing Sheets

OTHER PUBLICATIONS

Klibanov, A.L., et al, "A Two-Step Targeting Approach For Delivery of Doxorubicin-Loaded Liposomes To Tumour Cells In Vivo," Cancer Chemother. Pharmacol., 1995, pp. 91-101, vol. 36 (2), Germany.

Longman, S.A., et al., "Biotinylated pH-Sensitive Liposome Contains For Guided Administration of Biologically Active Substances To the Cells," Vestn Akad Med Navk, 1990, pp. 50-54, vol. 8, SSSR (USSR).

* cited by examiner

ENHANCED ULTRASOUND DETECTION WITH TEMPERATURE-DEPENDENT CONTRAST AGENTS

BACKGROUND OF THE INVENTION (1) Field of the Invention

This invention relates generally to ultrasound detection and imaging and, more particularly, to novel compositions, methods and devices for detecting a change in ultrasound reflectivity based upon changing the temperature of a temperature-dependent contrast agent bound to the target.

(2) Description of the Related Art

Molecular imaging can enhance the utility of traditional clinical imaging by allowing specific detection of molecular markers in tissues using site-targeted contrast agents (Weissleder, *Radiology* 212:609–614, 1999). Three approaches to site-targeted ultrasonic agents have been reported and these are based upon the use of liposomes (Alkan-Onyuksel et al., *J. Pharm. Sci* 85:486–490, 1996; Demos et al., *J. Pharm. Sci.* 86:167–171, 1997; Demos et al., *J. Am. Col. Cardiol.* 33:867–875, 1999), the use of microbubbles (Mattrey et al, *Am. J. Cardiol.* 54:206–210, 1984; Unger et al., *Am. J. Cardiol.* 81:58G–61G, 1998; Villanueva et al, *Circulation* 98:1–5, 1998; Klibanov et al, *Acad. Radiol.* 5S243–S246, 1998) or the use of nano-emulsions (Lanza et al, *Circulation* 94:3334–3340, 1996; Lanza et al, *J. Acoust. Soc. Am.* 104:3665–3672, 1998; Lanza et al, *Ultrasound Med. Biol.* 23: 863–870, 1997). Liposomes are spherical bimembrane vesicles produced spontaneously by phospholipids in water. Multilamellar lipid bilayers produced through a dehydration-rehydration process can form internal vesicles within a liposome and lead to increased acoustic reflectance (Alkan-Onyuksel et al., 1996 supra; Demos et al., 1997, supra; Demos et al., 1999, supra). In the second approach, microbubbles have been proposed for site-targeted modalities in addition to their perfusion applications. Microbubbles have been targeted towards thrombi (Unger et al., 1998 supra; Lanza et al., *Ultrasound. Med. Biol.* 23: 863–870, 1997), avidin-coated petri dish (Klibanov et al, 1998, supra) and activated endothelial cells (Villanueva et al, 1998, supra). Other investigators have examined the interaction of thrombus with site targeted agents. In particular, Unger et al. has observed successful binding of MRX-408, a bubble-based contrast agent, both in vitro and in vivo (Unger et al., 1998, supra).

The site-targeted nano-emulsions are nongaseous acoustic contrast agents made up of lipid-encapsulated liquid perfluorocarbon nanoparticules (see Lanza et al., U.S. Pat. Nos. 5,690,907; 5,780,010; and 5,958,371). The nanoparticles are approximately 250 nm in diameter. Perfluorocarbon nano-patriculate emulsions have been shown to provide substantial acoustic contrast when targeted towards in vitro and in vivo thrombi preparations (Lanza et al., 1998, supra; Lanza et al., 1997, supra).

One of the challenges confronting the use of site-targeted contrast agents is the sensitive detection and differentiation of the particles from the surrounding soft tissue. Detection of pathological changes on or near vascular surfaces may be compromised because the targeted substrate itself is echogenic or the signal from that surface may be somewhat view or angle dependent. Imaging techniques have been developed in attempts to solve this issue. Second harmonic or harmonic and power harmonic Doppler imaging has been used to allow differentiation of microbubbles in circulation from tissue (see Burns et al. *Clinical Radiol.* 51:50–55, 1996; Kasprzak et al, *Am. J. Cardiol.* 83:211–217, 1999; Senior et al, *Am. Heart J.* 139:245–251, 2000; Spencer et al, *J. Am. Soc. Echo.* 13:131–138, 2000). However, soft tissue also exhibits a second harmonic backscattered signal. Furthermore, the contrast agent may manifest velocities too slow for the sensitivity of Doppler techniques. Unlike the resonance phenomenon responsible for enhanced backscatter cross section in microbubbles, the mechanism for increased reflection enhancement from the site-targeted nanoparticle emulsions has been reported to be due to acoustic impedance mismatch at the surface where the particles bind (Lanza et al., 1998, supra). Thus, although site-targeted acoustic contrast agents and, in particular, the nano-emulsion contrast agents have been used as contrast agents, the development of approaches that produce a greater degree of contrast could potentially provide further sensitivity for ultrasound molecular imaging systems.

Perfluorocarbon liquids are known to transmit ultrasound at low velocities (Lagemann et al. *J. Am. Chem Soc.* 70: 2994–2996, 1948; Gupta, *Acustica* 42:273–277, 1979). The low ultrasound velocities through these substances have been shown to be temperature dependent in that the ultrasound velocity is decreased in a linear manner with increasing temperature (Narayana et al., *Acoustics Letters* 9:137–143, 1986). This observation was reported to be potentially applicable to the development of acoustic lenses (Id.). Nevertheless, the temperature-dependence of ultrasound velocity in perfluorocarbon liquids has not, heretofore, been suggested to have any applicability in ultrasound imaging systems.

Ultrasound energy has been applied in site-targeted contrast agents in ultrasound imaging methods as noted above. Much of this earlier work was directed to molecular imaging so that only low level ultrasound energy was used and no change in temperature of the targeted surface was reported to occur. In microbubble ultrasound imaging systems, sufficient energy has been applied to a liquid precursor substance to form gaseous microbubbles. (Lohrmann et al., U.S. Pat. No. 5,536,489; Unger, U.S. Pat. No. 5,542,935). One suggested approach has been to apply the energy to produce the phase shift in vivo. In such approaches, temperature changes would serve to convert the gaseous precursor to the gaseous microbubbles and none of these earlier studies disclosed or suggested changing temperature of an ultrasound contrast agent which remains in the liquid state or using the change in temperature of a nongaseous contrast agent as a basis for enhancing ultrasound detection.

Thus, there remains a continuing need for developing approaches that produce an enhanced degree of contrast and provide further sensitivity for ultrasound molecular imaging systems.

BRIEF SUMMARY OF THE INVENTION

Accordingly, the inventors herein have succeeded in discovering that changing the temperature of nanoparticles which contain a nongaseous fluorocarbon liquid and which are bound to a target, produces a detectable change in acoustic reflectivity of the target. Non-targeted regions which are adjacent to the target, but are not bound by the nanoparticles, show little or no detectable change in acoustic reflectivity. As a result, the temperature-dependent change in acoustic reflectivity of site-targeted nanoparticles provides a sensitive measurement of ultrasound reflectivity and provides enhanced contrast imaging.

Thus, in one embodiment, the present invention is directed to a method for changing acoustic reflectivity of an ultrasound target. The method comprises (1) administering to the target, a nongaseous acoustic imaging substance which binds to the target and produces a change in acoustic reflectivity with a change in temperature and (2) changing the temperature to produce a measurable change in acoustic reflectivity of the nongaseous acoustic imaging substance bound to the target. The nongaseous acoustic imaging substance, preferably, comprises a nanoparticle emulsion which contains a liquid fluorocarbon. The nongaseous acoustic imaging substance, preferably, comprises a ligand which binds to the target.

In another embodiment, the present invention comprises a method for measuring enhanced acoustic reflectivity of an ultrasound target. The method comprises (1) administering to the target, a nongaseous acoustic imaging substance which binds to the target and produces a change in acoustic reflectivity with a change in temperature and (2) changing the temperature to produce a measurable change in acoustic reflectivity of the nongaseous acoustic imaging substance bound to the target, and (3) detecting change in acoustic reflectivity of the bound substance. Detecting the change in acoustic reflectivity, preferably, comprises (a) measuring reflectivity prior to changing the temperature of the bound substance; (b) measuring reflectivity after changing the temperature of the bound substance; and (c) determining the change in reflectivity after changing the temperature of the bound substance compared to reflectivity prior to changing the temperature of the bound substance.

Another embodiment of the present invention involves a method for monitoring temperature of a tissue in a patient. The method comprises (1) administering to the patient, a nongaseous acoustic imaging substance which binds to the tissue and changes acoustic reflectivity with changes in temperature, (2) detecting acoustic reflectivity of the nongaseous acoustic imaging substance bound to the tissue (3) calculating temperature of the nongaseous acoustic imaging substance bound to the tissue. Preferably, the method monitors a change in temperature and the method further comprises changing the temperature of the tissue and the nongaseous acoustic imaging substance bound to the tissue. Detecting acoustic reflectivity comprises detecting the change in acoustic reflectivity of the nongaseous acoustic imaging substance bound to the tissue.

In one aspect of the present invention, the change in temperature can be produced by energizing the bound nongaseous nanoparticles to increase temperature of the bound substance and enhance acoustic reflectivity of the target. The nanoparticles can be energized by ultrasound, shortwave, microwave, magnetic radiation, electromagnetic energy or a combination thereof.

In another aspect of the present invention, the temperature of the bound nanoparticles can be decreased to produce a measurable decrease in acoustic reflectivity of the target.

The methods of the present invention can be used in conjunction with administration with a biologically active agent which is incorporated into the nanoparticle. In addition, other imaging techniques can be used with the acoustic imaging upon incorporating into the nanoparticle one or more imaging agents suitable for use in such other imaging techniques such as, for example, magnetic resonance imaging, electron spin resonance imaging, spectroscopic imaging, positron emission tomography imaging, optical imaging, x-ray imaging, nuclear medicine imaging or a combination thereof.

In another embodiment, the present invention comprises a device for measuring changes in temperature of a target to which a temperature-sensitive acoustic imaging substance is bound. The device comprises a component configured to change the temperature of the acoustic imaging substance, an ultrasound source configured to transmit acoustic energy to the target, an ultrasound detecting component configured to measure acoustic reflectivity of the surface and a comparator which determines acoustic reflectivity of the target upon changing temperature relative to acoustic reflectivity of the target in absence of changing temperature. In one aspect, the comparator determines difference in acoustic reflectivity of the target prior to and after changing temperature of the acoustic imaging substance bound to the target. In another aspect, the comparator determines the difference in acoustic reflectivity of the target upon changing temperature of the acoustic imaging substance bound to the target, compared to acoustic reflectivity of the target after the changed temperature of the acoustic imaging substance bound to the target is diminished. The temperature changing component can comprise an energy source which increases the temperature of acoustic imaging substance bound to the target or an energy absorbing component which decreases the temperature of the acoustic imaging substance bound to the target.

The device can also comprise a component which performs at least one other imaging technique such as, for example, magnetic resonance imaging, electron spin resonance imaging, spectroscopic imaging, positron emission tomography imaging, optical imaging, x-ray imaging nuclear medicine imaging or a combination thereof.

Among the several advantages achieved by the present invention, therefore, may be noted the provision of methods for enhancing acoustic reflectivity of a target; the provision of methods for distinguishing a target tissue from surrounding tissue which is acoustically reflective; the provision of methods for detecting and monitoring temperature of a tissue; the provision of methods for detecting temperature changes in a tissue such as during a therapeutic treatment involving a change in temperature; and the provision of devices for performing such methods.

DETAILED DESCRIPTION OF THE INVENTION

Figure 1:
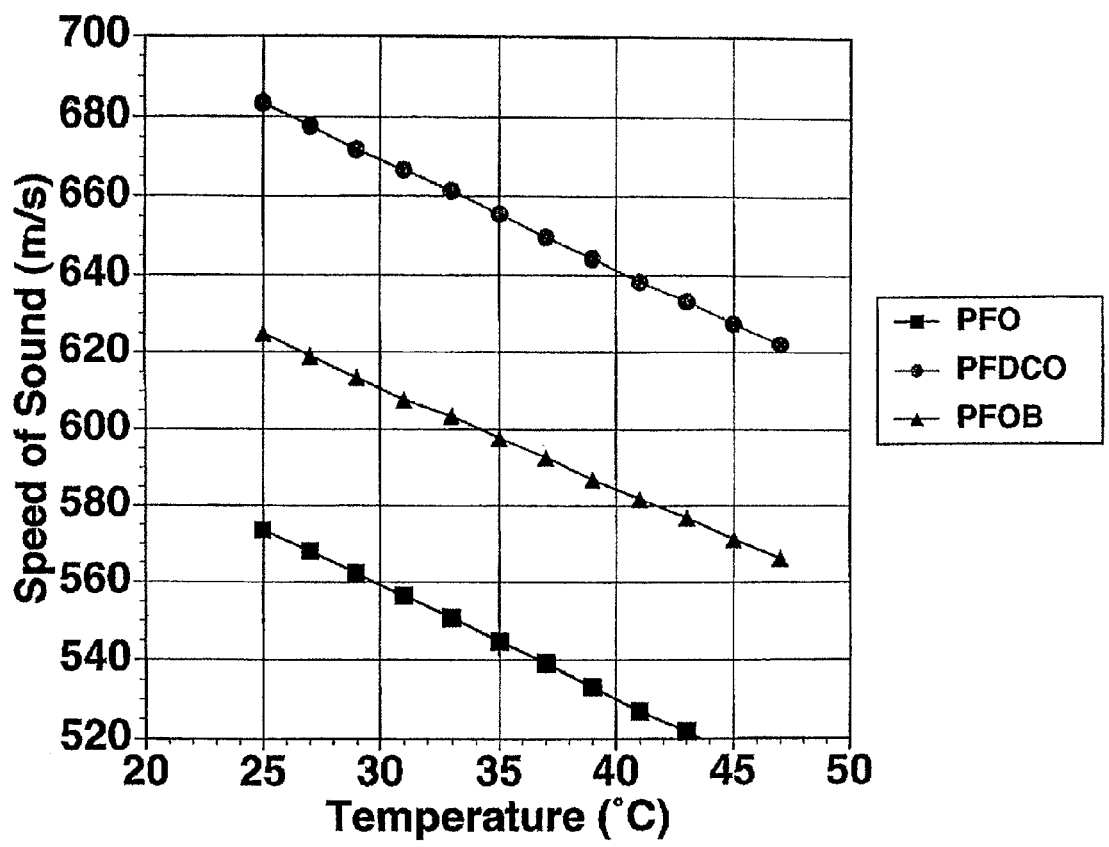
FIG. 1 illustrates the decrease in the speed of sound transmission with increasing temperatures for the perfluorocarbons, perfluorooctane (PFO), perfluorodichlorooctane (PFDCO) and perfluorooctylbromide (PFOB).

In accordance with the present invention, it has been discovered that the detection of acoustic reflectivity of an ultrasound target can be enhanced by changing the temperature of a nongaseous acoustic imaging substance which is bound to the target and which exhibits a measurable change in acoustic reflectivity with a change in temperature.

The acoustic imaging substance is, preferably, a nanoparticle emulsion as has been described earlier (see U.S. Pat. Nos. 5,780,010, 5,958,371 and 5,989,520). The nanoparticle emulsions of the present invention are comprised of at least two immiscible liquids which are intimately dispersed, preferably, a hydrophobic material such as an oil, dispersed in water. The emulsions are in the form of droplets or nanoparticles having a diameter which typically exceeds 0.1 μ. Additives such as surface-active agents or finely-divided solids can be incorporated into the emulsion nanoparticles to increase their stability.

The oil phase of the oil-in-water emulsion comprises, preferably, 5 to 50% and, more preferably 20 to 40% by weight of the emulsion. The oil or hydrophobic constituent exhibits an acoustic impedance that varies with changes (i.e. positively or negatively) in temperature, preferably, a fluorochemical liquid. These include straight, branched chain and cyclic perfluorocarbons, straight, branched chain and cyclic perfluoro tertiary amines, straight, branched chain and cyclic perfluoro ethers and thioethers, chlorofluorocarbons and polymeric perfluoro ethers and the like. Although up to 50% hydrogen-substituted compounds can be used, perhalo compounds are preferred. Most preferred are perfluorinated compounds. Any fluorochemical liquid, i.e. a substance which is a liquid at or above body temperature (e.g. 37° C.) at atmospheric pressure, can be used to prepare a fluorochemical emulsion of the present invention. However, for many purposes emulsions of fluorochemicals with longer extended stability are preferred. In order to obtain such emulsions, fluorochemical liquids with boiling points above 50° C. are preferred, and most preferred are fluorochemical liquids with boiling points above about 80° C. The guiding determinant should be that the oil, e.g. a fluorochemical, should be expected to remain in a liquid phase (less than 10% gas conversion) under the intended conditions of themal induction and imaging.

Reference to the term "nongaseous" or "liquid " in the context of the nanoparticle emulsions of the present invention is intended to mean that less than 10% of the interior volume of the nanoparticles is in a gas phase per total volume of the nanoparticles (i.e. v/v), more preferably, no more than about 8% (v/v), more preferably no more than about 5% (v/v), and most preferably, no more than than 2% (v/v) or less. The term "about" as used herein is intended to encompass a range of values 10% above and below a stated value such that, for example, about 8% is intended to encompass the range of values from 7.2% to 8.8%.

The nanoparticle emulsions of the present invention are, preferably, lipid encapsulated. In a specific example, the lipid encapsulated particles may be constituted by a perfluorocarbon emulsion, the emulsion particles having an outer coating of a derivatized natural or synthetic phospholipid, a fatty acid, cholesterol, lipid, sphingomyelin, tocopherol, glucolipid, sterylamine, cardiolipin, a lipid with ether or ester linked fatty acids or a polymerized lipid.

Fluorocarbon emulsions and, in particular, perfluorocarbon emulsions are well suited for biomedical applications and for use in the practice of the present invention. The perfluorocarbon emulsions are known to be stable, biologically inert and readily metabolized, primarily by transpulmonic alveolae evaporation. Further, their small particle size easily accommodates transpulmonic passage and their circulatory half-life (4–8 hours) advantageously exceeds that of other agents. Also, perfluorocarbons have been used to date in a wide variety of biomedical applications, including use as artificial blood substitutes. For use in the present invention, various fluorocarbon emulsions may be employed including those in which the fluorocarbon is a fluorocarbon-hydrocarbon, a perfluoroalkylated ether, polyether or crown ether. Useful perfluorocarbon emulsions are disclosed in U.S. Pat. Nos. 4,927,623, 5,077,036, 5,114,703, 5,171,755, 5,304,325, 5,350,571, 5,393,524, and 5,403,575 and include those in which the perfluorocarbon compound is perfluorotributylamine, perfluorodecalin, perfluorooctylbromide, perfluorodichlorooctane, perfluorodecane, perfluorotripropylamine, perfluorotrimethylcyclohexane or other perfluorocarbon compounds. Further, mixtures of such perfluorocarbon compounds may be incorporated in the emulsions utilized in the practice of the invention.

As a specific example of a perfluorocarbon emulsion useful in the invention may be mentioned a perfluorodichlorooctane emulsion wherein the lipid coating thereof contains between approximately 50 to 99.5 mole percent lecithin, preferably approximately 55 to 70 to mole percent lecithin, 0 to 50 mole percent cholesterol, preferably approximately 25 to 45 mole percent cholesterol and approximately 0.5 to 10 mole percent biotinylated phosphatidylethanolamine, preferably approximately 1 to 5 mole percent biotinylated phosphatidylethanolamine. Other phospholipids such as phosphatidylserine may be biotinylated, fatty acyl groups such as stearylamine may be conjugated to biotin, or cholesterol or other fat soluble chemicals may be biotinylated and incorporated in the lipid coating for the lipid encapsulated particles. The preparation of an exemplary biotinylated perfluorocarbon for use in the practice of the invention is described hereinafter in accordance with known procedures.

When the lipid encapsulated particles are constituted by a liposome rather than an emulsion, such a liposome may be prepared as generally described in the literature (see, for example, Kimelberg et al., *CRC Crit. Rev. Toxicol.* 6:25, 1978; Yatvin et al., *Medical Physics* 9:149, 1982). Liposomes are known to the art and generally comprise lipid materials including lecithin and sterols, egg phosphatidyl choline, egg phosphatidic acid, cholesterol and alpha-tocopherol.

Emulsifying agents, for example surfactants, may be used to facilitate the formation of emulsions and increase their stability. Typically, aqueous phase surfactants have been used to facilitate the formation of emulsions of fluorochemical liquids. A surfactant is any substance that contains both hydrophilic and a hydrophobic portions. When added to water or solvents, a surfactant reduces the surface tension. Preferred surfactants are phospholipids and cholesterol.

Any or a variety of lipid surfactants may be incorporated into the lipid monolayer preferably natural or synthetic phospholipids, but also fatty acids, cholesterols, lysolipids, sphingomyelins, tocopherols, glucolipids, stearylarnines, cardiolipins, plasmalogens, a lipid with ether or ester linked fatty acids, polymerized lipids, and lipid conjugated polyethylene glycol. Other known surfactant additives such as PLURONIC F-68, HAMPOSYL L30 (W. R. Grace Co., Nashua, N.H.), sodium dodecyl sulfate, Aerosol 413 (American Cyanamid Co., Wayne, N.J.), Aerosol 200 (American Cyanamid Co.), LIPOPROTEOL LCO (Rhodia Inc., Mammoth, N.J.), STANDAPOL SH 135 (Henkel Corp., Teaneck, N.J.), FIZUL 10-127 (Finetex Inc., Elmwood Park, N.J.), and CYCLOPOL SBFA 30 (Cyclo Chemicals Corp., Miami, Fla.); amphoterics, such as those sold with the trade names: Deriphat.TM. 170 (Henkel Corp.), LONZAINE JS (Lonza, Inc.), NIRNOL C2N-SF (Miranol Chemical Co., Inc., Dayton, N.J.), AMPHOTERGE W2 (Lonza, Inc.), and AMPHOTERGE 2WAS (Lonza, Inc.); non-ionics, such as those sold with the trade names: PLURONIC F-68 (BASF Wyandotte, Wyandotte, Mich.), PLURONIC F-127 (BASF Wyandotte), BRIJ 35 (ICI Americas; Wilmington, Del.), TRITON X-100 (Rohm and Haas Co., Philadelphia, Pa.), BRIJ 52 (ICI Americas), SPAN 20 (ICI Americas), GENEROL 122 ES (Henkel Corp.), TRITON N-42 (Rohm and Haas Co.,), Triton.TM. N-101 (Rohm and Haas Co.,), TRITON X-405 (Rohm and tlaas Co.,), TWEEN 80 (ICI Americas), TWEEN 85 (ICI Americas), and BRIJ 56 (ICI Americas) and the like, may be used alone or in combination in amounts of 0.10 to 5.0% by weight to assist in stabilizing the emulsions.

Fluorinated surfactants which are soluble in the fluorochemical liquid to be emulsified can also be used. Suitable fluorochemical surfactants include perfluorinated alkanoic acids such as perfluorohexanoic and perfluorooctanoic acids and amidoamine derivatives. These surfactants are generally used in amounts of 0.01 to 5.0% by weight, and preferably in amounts of 0.1 to 1.0%. Other suitable fluorochemical surfactants include perfluorinated alcohol phosphate esters and their salts; perfluorinated sulfonamide alcohol phosphate esters and their salts; perfluorinated alkyl sulfonamide alkylene quaternary ammonium salts; N,N(carboxyl-substituted lower alkyl) perfluorinated alkyl sulfonamides; and mixtures thereof. As used herein, the term "perfluorinated" means that the surfactant contains at least one perfluorinated alkyl group.

Suitable perfluorinated alcohol phosphate esters include the free acids of the diethanolamine salts of mono- and bis(1H, 1H, 2H, 2H-perfluoroalkyl)phosphates. The phosphate salts, available under the tradename ZONYL RP (E. I. Dupont de Nemours and Co., Wilmington, Del.), are converted to the corresponding free acids by known methods. Suitable perfluorinated sulfonamide alcohol phosphate esters are described in U.S. Pat. No. 3,094,547. Suitable perfluorinated sulfonamide alcohol phosphate esters and salts of these include perfluoro-n-octyl-N-ethylsulfonamidoethyl phosphate, bis(perfluoro-n-octyl-N-ethylsulfonamidoethyl) phosphate, the ammonium salt of bis(perfluoro-n-octyl-N-ethylsulfonamidoethyl)phosphate, bis (perfluorodecyl-N-ethylsulfonamidoethyl)-phosphate and bis(perfluorohexyl-N ethylsulfonamidoethyl)-phosphate. The preferred formulations use phosphatidylcholine, derivatized-phosphatidylethanolamine and cholesterol as the aqueous surfactant.

Lipid encapsulated emulsions may be formulated with cationic lipids in the surfactant layer that facilitate the adhesion of nucleic acid material to particle surfaces. Cationic lipids may include but are not limited to 1,2-Diacyl-3-Trimethylammonium-Propane (TAP), 1,2-Diacyl-3-Dimethylammonium-Propane (DAP), DC-Cholesterol (DC-Chol), Dimethyldioctadecylammonium Bromide (DDAB), 1,2-Diacyl-sn-Glycero-3-Ethylphosphocholine DOTMA, N-[1-(2,3-dioleoyloxy)propyl]-N,N,N-trimethylammoium chloride; DOTAP, 1,2-dioleoyloxy-3-(trimethylammonio) propane; and DOTB, 1,2-dioloyl-3-(4'-trimethyl-ammonio) butanoyl-sn-glycerol may be used. In general the molar ratio of cationic lipid to non-cationic lipid in the lipid surfactant monolayer may be, for example, 1:1000 to 2:1, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid component of the emulsion surfactant, particularly dipalmitoylphosphatidylcholine, dipalmitoylphosphatidyl-ethanolamine or dioleoylphosphatidylethanolamine in addition to those previously described. In lieu of cationic lipids as described above, lipids bearing cationic polymers such as polylysine or polyarginine may also be included in the lipid surfactant and afford binding of a negatively charged therapeutic, such as genetic material or analogues there of, to the outside of the emulsion particles.

The acoustic contrast substances of the present invention, which are preferably comprised of at least one perfluorocarbon, exhibit a temperature dependent reflectivity when bound to a targert. Perfluorocarbons have been reported to show a linear decrease in ultrasonic velocity with rise in temperature and a decrease in density over temperature ranges of as low as 10° C. to as high as 50° C. (Narayana et al., supra, 1986). Thus, the temperature dependence of the nanoparticle emulsion or that of its constituent components, such as for example the preferred perfluorocarbon component, can be measured by determining ultrasound velocity of the emulsion or constituent component as is illustrated more fully below in the examples. It is believed that this measurement can also be used to predict the magnitude of change in reflectivity for a given perfluorocarbon component.

The ultrasound target may be an in vivo or in vitro target and, preferably, a biological material although the target need not be a biological material. The target may be comprised of a surface to which the acoustic contrast substance binds or a three dimensional structure in which the acoustic contrast substance penetrates and binds to portions of the target below the surface.

Preferably, a ligand is incorporated into the acoustic contrast substance to immobilize the acoustic contrast substance to the ultrasound target. The ligand may be specific for a desired target to allow active targeting. Active targeting refers to ligand-directed, site-specific accumulation of agents to cells, tissues or organs by localization and binding to molecular epitopes, i.e., receptors, lipids, peptides, cell adhesion molecules, polysaccharides, biopolymers, and the like, presented on the surface membranes of cells or within the extracellular or intracellular matrix. A wide variety of ligands can be used including an antibody, a fragment of an antibody, a polypeptide such as small oligopeptide, a large polypeptide or a protein having three dimensional structure, a peptidomimetic, a polysaccharide, an aptamer, a lipid, a nucleic acid, a lectin or a combination thereof. The ligand specifically binds to a cellular epitope or receptor.

The term "ligand" as used herein is intended to refer to a small targeting molecule that binds specifically to another molecule of a biological target separate and distinct from the emulsion particle itself. The reaction does not require nor exclude a molecule that donates or accepts a pair of electrons to form a coordinate covalent bond with a metal atom of a coordination complex. Thus a ligand may be attached covalently for direct-conjugation or noncovalently for indirect conjugation to the surface of the acoustic particle surface.

Avidin-biotin interactions are extremely useful, noncovalent targeting systems that have been incorporated into many biological and analytical systems and selected in vivo applications. Avidin has a high affinity for biotin ($10^{-15}$M) facilitating rapid and stable binding under physiological conditions. Targeted systems utilizing this approach are administered in two or three steps, depending on the formulation. Typically, a biotinylated ligand, such as a monoclonal antibody, is administered first and "pretargeted" to the unique molecular epitopes. Next, avidin is administered, which binds to the biotin moiety of the "pretargeted" ligand. Finally, the biotinylated agent is added and binds to the unoccupied biotin-binding sites remaining on the avidin thereby completing the ligand-avidin-emulsion "sandwich". The avidin-biotin approach can avoid accelerated, premature clearance of targeted agents by the reticuloendothelial system secondary to the presence of surface antibody. Additionally, avidin, with four, independent biotin binding sites provides signal amplification and improves detection sensitivity.

As used herein, the term "biotin agent" or "biotinylated" with respect to conjugation to a biotin agent is intended to include biotin, biocytin and other biotin derivatives and analogs such as biotin amido caproate N-hydroxysuccinimide ester, biotin 4-amidobenzoic acid, biotinamide caproyl hydrazide and other biotin derivatives and conjugates. Other derivatives include biotin-dextran, biotin-disulfideN-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides and biotinylated amino acids such as N, $\epsilon$-biotinyl-1-lysine. The term "avidin agent" or "avidinized" with respect to conjugation to an avidin agent is intended to include avidin, streptavidin and other avidin analogs such as streptavidin or avidin conjugates, highly purified and fractionated species of avidin or streptavidin, and non-amino acid or partial-amino acid variants, recombinant or chemically synthesized avidin.

Targeting ligands may be chemically attached to the surface of acoustic particles by a variety of methods depending upon the nature of the particle surface. Conjugations may be performed before or after the emulsion particle is created depending upon the ligand employed. Direct chemical conjugation of ligands to proteinaceous agents often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for ligand conjugation after the particles are formed. Another common post-processing approach is to activate surface carboxylates with carbodiimide prior to ligand addition. The selected covalent linking strategy is primarily determined by the chemical nature of the ligand. Monoclonal antibodies and other large proteins may denature under harsh processing conditions; whereas, the bioactivity of carbohydrates, short peptides, aptamers, drugs or peptidomimetics often can be preserved. To ensure high ligand binding integrity and maximize targeted particle avidity flexible polymer spacer arms, e.g. polyethylene glycol or simple caproate bridges, can be inserted between an activated surface functional group and the targeting ligand. These extensions can be 10 nm or longer and minimize interference of ligand binding by particle surface interactions.

Monoclonal antibodies may also be used as site-targeting ligands directed to any of a wide spectrum of molecular epitopes including pathologic molecular epitopes. Immunoglobin-$\gamma$ (IgG) class monoclonal antibodies have been conjugated to liposomes, emulsions and other microbubble particles to provide active, site-specific targeting. These proteins are symmetric glycoproteins (MW ca. 150,000 Daltons) composed of identical pairs of heavy and light chains. Hypervariable regions at the end of each of two arms provide identical antigen-binding domains. A variably sized branched carbohydrate domain is attached to complement-activating regions, and the hinge area contains particularly accessible interchain disulfide bonds that may be reduced to produce smaller fragments.

Bivalent F(ab')$_2$ and monovalent F(ab) fragments can be used as ligands and these are derived from selective cleavage of the whole antibody by pepsin or papain digestion, respectively. Elimination of the Fc region greatly diminishes the immunogenicity of the molecule, diminishes nonspecific liver uptake secondary to bound carbohydrate, and reduces complement activation and resultant antibody-dependent cellular toxicity. Complement fixation and associated cellular cytotoxicity can be detrimental when the targeted site must be preserved or beneficial when recruitment of host killer cells and target-cell destruction is desired (e.g. anti-tumor agents).

Most monoclonal antibodies are of murine origin and are inherently immunogenic to varying extents in other species. Humanization of murine antibodies through genetic engineering has lead to development of chimeric ligands with improved biocompatibility and longer circulatory half-lives. The binding affinity of recombinant antibodies to targeted molecular epitopes can be occasionally improved with selective site-directed mutagenesis of the binding idiotype.

Phage display techniques may be used to produce recombinant human monoclonal antibody fragments against a large range of different antigens without involving antibody-producing animals. In general, cloning creates large genetic libraries of corresponding DNA (cDNA) chains deducted and synthesized by means of the enzyme "reverse transcriptase" from total messenger RNA (MRNA) of human B lymphocytes. Immunoglobulin cDNA chains are amplified by PCR (polymerase chain reaction) and light and heavy chains specific for a given antigen are introduced into a phagemid vector. Transfection of this phagemid vector into the appropriate bacteria results in the expression of an scFv immunoglobulin molecule on the surface of the bacteriophage. Bacteriophages expressing specific immunoglobulin are selected by repeated immunoadsorption/phage multiplication cycles against desired antigens (e.g., proteins, peptides, nuclear acids, and sugars). Bacteriophages strictly specific to the target antigen are introduced into an appropriate vector, (e.g., *Escherichia coli*, yeast, cells) and amplified by fermentation to produce large amounts of human antibody fragments with structures very similar to natural antibodies. Phage display techniques have permitted the production of unique ligands for targeting and therapeutic applications.

Polypeptides, like antibodies, may have high specificity and epitope affinity for use as vector molecules for targeted contrast agents. These may be small oligopeptides, having, for example, 5 to 10 amino acid, specific for a unique receptor sequences (such as, for example, the RGD epitope of the platelet GIIbIIIa receptor) or larger, biologically active hormones such as cholecystokinin. Smaller peptides potentially have less inherent immunogenicity than nonhumanized murine antibodies. Peptides or peptide (nonpeptide) analogues of cell adhesion molecules, cytokines, selectins, cadhedrins, Ig superfamily, integrins and the like may be utilized for targeted therapeutic delivery.

Asialoglycoproteins have been used for liver-specific applications due to their high affinity for asialoglycoproteins receptors located uniquely on hepatocytes. Asialoglycoproteins directed agents (primarily magnetic resonance agents conjugated to iron oxides) have been used to detect primary and secondary hepatic tumors as well as benign, diffuse liver disease such as hepatitis. The asialoglycoproteins receptor is highly abundant on hepatocytes, approximately 500,000 per cell, rapidly internalizes and is subsequently recycled to the cell surface. Polysaccharides such as arabinogalactan may also be utilized to localize agents to hepatic targets. Arabinogalactan has multiple terminal arabinose groups that display high affinity for asialoglycoproteins hepatic receptors.

Aptamers are high affinity, high specificity RNA or DNA-based ligands produced by in vitro selection experiments (SELEX: systematic evolution of ligands by exponential enrichment). Aptamers are generated from random sequences of 20 to 30 nucleotides, selectively screened by absorption to molecular antigens or cells, and enriched to purify specific high affinity binding ligands. To enhance in vivo stability and utility, aptamers are generally chemically modified to impair nuclease digestion and to facilitate conjugation with drugs, labels or particles. Other, simpler chemical bridges often substitute nucleic acids not specifically involved in the ligand interaction. In solution aptamers are unstructured but can fold and enwrap target epitopes providing specific recognition. The unique folding of the nucleic acids around the epitope affords discriminatory intermolecular contacts through hydrogen bonding, electrostatic interaction, stacking, and shape complementarity. In comparison with protein-based ligands, aptamers are stable, are more conducive to heat sterilization, and have lower immunogenicity. Aptamers are currently used to target a number of clinically relevant pathologies including angiogenesis, activated platelets, and solid tumors and their use is increasing. The clinical effectiveness of aptamers as targeting ligands for therapeutic emulsion particles may be dependent upon the impact of the negative surface charge imparted by nucleic acid phosphate groups on clearance rates. Previous research with lipid-based particles suggest that negative zeta potentials markedly decrease liposome circulatory half-life, whereas, neutral or cationic particles have similar, longer systemic persistence.

It is also possible to use what has been referred to as a "primer material" to couple specific binding species to the fluorchemical droplets as disclosed by Millbrath et al. (U.S. Pat. No. 5,401,634) for certain in vitro applications. As used herein, "primer material" refers to any constituent or derivatized constituent incorporated into the emulsion lipid surfactant layer that could be chemically utilized to form a covalent bond between the particle and a targeting ligand or a component of the targeting ligand such as a subunit thereof.

Thus, the specific binding species (i.e. targeting ligand) may be immobilized on the encapsulating lipid monolayer by direct adsorption to the oil/aqueous interface or using a primer material. A primer material may be any surfactant compatible compound incorporated in the particle to chemically couple with or adsorb a specific binding or targeting species. The preferred result is achieved by forming an emulsion with an aqueous continuous phase and a biologically active ligand adsorbed or conjugated to the primer material at the interface of the continuous and discontinuous phases. Naturally occurring or synthetic polymers with amine, carboxyl, mercapto, or other functional groups capable of specific reaction with coupling agents and highly charged polymers may be utilized in the coupling process. The specific binding species (e.g. antibody) may be immobilized on the fluorochemical emulsion particle surface by direct adsorption or by chemical coupling. Examples of specific binding species which can be immobilized by direct adsorption include small peptides, peptidomimetics, or polysaccharide-based agents. To make such an emulsion the specific binding species may be suspended or dissolved in the aqueous phase prior to formation of the emulsion. Alternatively, the specific binding species may be added after formation of the emulsion and incubated with gentle agitation at room temperature (25° C.) in a pH 7.0 buffer (typically phosphate buffered saline) for 1.2 to 18 hours.

Where the specific binding species is to be coupled to a primer material, conventional coupling techniques may be used. The specific binding species may be covalently bonded to primer material with coupling agents using methods which are known in the art. Primer materials may include phosphatidylethanolamine (PE), N-caproylamine-PE, n-dodecanylamine, phosphatidylthioethanol, N-1,2-diacyl-sn-glycero-3-phosphoethanolamine-N-[4-(p-maleimidophenyl)butyramide], 1,2-diacyl-sn-glycero-3-phosphoethanolamine-N-[4-(p-maleimidomethyl)cyclohexane-carboxylate], 1,2-diacyl-sn-glycero-3-phosphoethanolamine-N-[3-(2-pyridyldithio)propionate], 1,2-diacyl-sn-glycero-3-phosphoethanolamine-N[PDP(polyethylene glycol)2000], N-succinyl-PE, N-glutaryl-PE, N-dodecanyl-PE, N-biotinyl-PE, or N-caproyl-PE. Additional coupling agents use a carbodiimide such as 1-ethyl-3-(3-N,N dimethylaminopropyl)carbodiimide hydrochloride or 1-cyclohexyl-3-(2-morpholinoethyl)carbodiimide methyl-p-toluenesulfonate. Other suitable coupling agents include aldehyde coupling agents having either ethylenic unsaturation such as acrolein, methacrolein, or 2-butenal, or having a plurality of aldehyde groups such as glutaraldehyde, prop anedial or butanedial. Other coupling agents include 2-iminothiolane hydrochloride, bifunctional N-hydroxysuccinimide esters such as disuccinimidyl subsrate, disuccinimidyl tartrate, bis[2-(succinimidooxycarbonyloxy)ethyl]sulfone, disuccinimidyl propionate, ethylene glycolbis(succinimidyl succinate); heterobifunctional reagents such as N-(5-azido-2-nitrobenzoyloxy)succinimide, p-azidophenylbromide, p-azidophenylglyoxal,4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, N-(4-azidophenylthio)phthalamide; homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Covalent bonding of a specific binding species to the primer material can be carried out with the above reagents by conventional, well-known reactions, for example, in the aqueous solutions at a neutral pH, at temperatures of less than 25 C for 1 hour to overnight.

The emulsions of the present invention may be prepared by various techniques. One method is sonication of a mixture of a fluorochemical liquid and an aqueous solution containing a suitable primer material and/or specific binding species. Generally, these mixtures include a surfactant. Cooling the mixture being emulsified, minimizing the concentration of surfactant, and buffering with a saline buffer will typically maximize both retention of specific binding properties and the coupling capacity of the primer material. These techniques provide excellent emulsions with high activity per unit of absorbed primer material or specific binding species.

When high concentrations of a primer material or specific binding species coated on lipid emulsions, the mixture should be heated during sonication and have a relatively low ionic strength and moderate to low pH. Too low an ionic strength, too low a pH or too much heat may cause some degradation or loss of all of the useful binding properties of the specific binding species or the coupling capacity of the "primer" material. Careful control and variation of the emulsification conditions can optimize the properties of the primer material or the specific binding species while obtaining high concentrations of coating.

Carbohydrate-bearing lipids may be employed for in vivo targeting, as described in U.S. Pat. No. 4,310,505, the disclosures of which are hereby incorporated herein by reference, in their entirety.

An alternative method of making the emulsions involves directing high pressure streams of mixtures containing the aqueous solution, a primer material or the specific binding species, the fluorocarbon liquid and a surfactant (if any) so that they impact one another to produce emulsions of narrow particle size and distribution. The MICROFLUIDIZER apparatus (Microfluidics, Newton, Mass.) can be used to make the preferred emulsions. The apparatus is also useful to post-process emulsions made by sonication or other conventional methods. Feeding a stream of emulsion droplets through the MICROFLUIDIZER apparatus yields formulations small size and narrow particle size distribution.

Emulsifying and/or solubilizing agents may also be used in conjunction with emulsions. Such agents include, but are not limited to, acacia, cholesterol, diethanolamine, glyceryl monostearate, lanolin alcohols, lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax. All lipids with perfluoro fatty acids as a component of the lipid in lieu of the saturated or unsaturated hydrocarbon fatty acids found in lipids of plant or animal origin may be used. Suspending and/or viscosity-increasing agents that may be used with emulsions include, but are not limited to, acacia, agar, alginic acid, aluminum mono-stearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

Useful emulsions may have a wide range of nominal particle diameters, e.g., from as small as about 0.01 µ to as large as 10 µ, preferably about 0.1 to about 0.5 µ in diameter. The emulsion particle sizes can be controlled and varied by modifications of the emulsification techniques and the chemical components. Small size particles are preferred because they circulate longer and tend to be more stable than larger particles.

Targeted therapeutic emulsions may incorporate bioactive agents (e.g drugs, prodrugs, genetic materials, radioactive isotopes, or combinations thereof) in their native form or derivatized with hydrophobic or charged moieties to enhance incorporation or adsorption to the ligand targeted particle. The bioactive agent may be a prodrug, including the prodrugs described, for example, by Sinkyla et al., J. Pharm. Sci., 64:181–210 (1975), in U.S. application Ser. No. 08/851,780 filed May 6, 1997, and in U.S. application Ser. No. 08/887,215 filed Jul. 2, 1997, the disclosures of which are hereby incorporated by reference herein in their entirety.

Such therapeutics may also include, but are not limited to antineoplastic agents, including platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin, bleomycin sulfate, methotrexate, adriamycin, arabinosyl, hydroxyurea, procarbazine, dacarbazine, mitotic inhibitors such as etoposide and other vinca alkaloids; radiopharmaceuticals such as but not limited to radioactive iodine, samarium, strontium cobalt, yttrium and the like; protein and nonprotein natural products or analogues/mimetics thereof including hormones such as but not limited to growth hormone, somatostatin, prolactin, thyroid, steroids, androgens, progestins, estrogens and antiestrogens; analgesics including but not limited to antirheumatics, such as auranofin, methotrexate, azathioprine, sulfazalazine, leflunomide, hydrochloroquine, and etanercept; muscle relaxants such as baclofen, dantrolene, carisoprodol, diazepam, metaxalone, cyclobenzaprine, chlorzoxazone, tizanidine; narcotic agonists such as codeine, fentanyl, hydromorphone, lleavorphanol, meperidine, methadone, morphine, oxycodone, oxymorphone, propoxyphene; narcotic agonist-antagonists such as buprenorphine, butorphanol, dezocine, nalbuphine, pentazocine; narcotic antagonists such as nalmefene and naloxone, other analgesics including ASA, acetominophen, tramadol, or combinations thereof; nonsteroidal anti-inflammatories including but not limited to celecoxib, diclofenac, diflunisal, etodolac, fenoprofen, flurbiprofen, ibuprofen, indomethacin, ketoprofen, ketorolac, naproxen, oxaproxen, rofecoxib, salisalate, suldindac, tolmetin; anesthetic and sedatives such as etomidate, fentanyl, ketamine, methohexital, propofol, sufentanil, thiopental, and the like; neuromuscular blockers such as but not limited to pancuronium, atracurium, cisatracurium, rocuronium, succinylcholine, vercuronium; antimicrobials including aminoglycosides, antifungal agents including amphotericin B, clotrimazole, fluconazole, flucytosine, griseofulvin, itraconazole, ketoconazole, nystatin, and terbinafine; anti-helmintics; antimalarials, such as chloroquine, doxycycline, mefloquine, primaquine, quinine; antimycobacterial including dapsone, ethambutol, ethionamide, isoniazid, pyrazinamide, rifabutin, rifampin, rifapentine; antiparasitic agents including albendazole, atovaquone, iodoquinol, ivermectin, mebendazole, metronidazole, pentamidine, praziquantel, pyrantel, pyrimethamine, thiabendazole; antiviral agents including abacavir, didanosine, lamivudine, stavudine, zalcitabine, zidovudine as well as protease inhibitors such as indinavir and related compounds, anti-CMV agents including but not limited to cidofovir, foscarnet, and ganciclovir; antiherpetic agents including amatadine, rimantadine, zanamivir; interferons, ribavirin, rebetron; carbapenems, cephalosporins, fluoroquinones, macrolides, penicillins, sulfonamides, tetracyclines, and other antimicrobials including aztreonam, chloramphenieol, fosfomycin, furazolidone, nalidixic acid, nitrofurantoin, vancomycin and the like; nitrates, antihypertensives including diuretics, beta blockers, calcium channel blockers, angiotensin converting enzyme inhibitors, angiotensin receptor antagonists, antiadrenergic agents, anti-dysrhythmics, antihyperlipidemic agents, antiplatelet compounds, pressors, thrombolytics, acne preparations, antipsoriatics; corticosteroids; androgens, anabolic steroids, bisphosphonates; sulfonoureas and other antidiabetic agents; gout related medicants; antihistamines, antitussive, decongestants, and expectorants; antiulcer medicants including antacids, 5-HT receptor antagonists, H2-antagonists, bismuth compounds, proton pump inhibitors, laxatives, octreotide and its analogues/mimetics; anticoagulants; immunization antigens, immunoglobins, immunosuppressive agents; anticonvulsants, 5-HT receptor agonists, other migraine therapies; parkinsonian agents including anticholinergics, and dopaminergics; estrogens, GnRH agonists, progestins, estrogen receptor modulators, tocolytics, uterotnics, thyroid agents such as iodine products and anti-thyroid agents; blood products such as parenteral iron, hemin, hematoporphyrins and their derivatives.

Genetic material, includes, for example, nucleic acids, RNA and DNA, of either natural or synthetic origin, including recombinant RNA and DNA and antisense RNA and DNA; hammerhead RNA, ribozymes, hammerhead ribozymes, antigene nucleic acids, both single and double stranded RNA and DNA and analogs thereof, ribooligonucleotides, antisense ribooligonucleotides, deoxyribooligonucleotides, and antisense deoxyribooligonucleotides. Other types of genetic material that may be used include, for example, genes carried on expression vectors such as plasmids, phagemids, cosmids, yeast artificial chromosomes, and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers.

As we have previously described, the emulsion nanoparticles may incorporate on the particle paramagnetic or super paramagnetic elements including but not limited to gadolinium, magnesium, iron, manganese in their native or in a chemically complexed form. Similarly, radioactive nuclides including positron-emitters, gamma-emitters, beta-emitters, alpha-emitters in their native or chemically-complexed form may be included on or in the particles. Adding of these moieties permits the additional use of other clinical imaging modalities such as magnetic resonance imaging, positron emission tomography, and nuclear medicine imaging techniques in conjunction with temperature enhanced ultrasonic imaging. Moreover, the inclusion of metal ions in or on the formulation may be utilized as "seeds" to augment or implement local hyperthermia.

In addition, optical imaging, which refers to the production of visible representations of tissue or regions of a patient produced by irradiating those tissues or regions of a patient with electromagnetic energy in the spectral range between ultraviolet and infrared, and analyzing either the reflected, scattered, absorbed and/or fluorescent energy produced as a result of the irradiation, may be combined with the enhanced acoustic reflectivity of temperature-dependent targeted emulsions. Examples of optical imaging include, but are not limited to, visible photography and variations thereof, ultraviolet images, infrared images, fluorimetry, holography, visible microscopy, fluorescent microscopy, spectrophotometry, spectroscopy, fluorescence polarization and the like.

Photoactive agents, i.e. compounds or materials that are active in light or that responds to light, including, for example, chromophores (e.g., materials that absorb light at a given wavelength), fluorophores (e.g., materials that emit light at a given wavelength), photosensitizers (e.g., materials that can cause necrosis of tissue and/or cell death in vitro and/or in vivo), fluorescent materials, phosphorescent materials and the like, that may be used in diagnostic or therapeutic applications. "Light" refers to all sources of light including the ultraviolet (UV) region, the visible region and/or the infrared (IR) region of the spectrum. Suitable photoactive agents that may be used in the present invention have been described by others (Unger et al U.S. Pat. No. 6,123,923) are incorporated by reference herein and include but are not limited to, for example, fluoresceins, indocyanine green, rhodamine, triphenylmethines, polymethines, cyanines, fullerenes, oxatellurazoles, verdins, rhodins, perphycenes, sapphyrins, rubyrins, cholesteryl 4,4-difluoro-5,7-dimethyl-4-bora-3a,4a-diaza-s-indacene-3-dodecanoate, cholesteryl 12-(N-methyl-N-(7-nitrobenz-2-oxa-1,3-diazol-4-yl)amino)-dodecanate, cholesteryl cis-parinarate, cholesteryl 3-((6-phenyl)-1,3,5-hexatrienyl)phenyl-proprionate, cholesteryl 1-pyrenebutyrate, cholesteryl 1-pyrenedecanoate, cholesteryl 1-pyrenehexanoate, 22-(N-(7-nitrobenz-2-oxa-1,3-diazol-4-yl)amino)-23,24-bisnor-5-cholen-3.beta.-ol, 22-(N-(7-nitrobenz-2-oxa-1,3-diazol-4-yl)amino)-23,24-bisnor-5-cholen-3.beta.-yl cis-9-octadecenoate, 1-pyrenemethyl3-(hydroxy-22,23-bisnor-5-cholenate, 1-pyrene-methyl 3.beta.-(cis-9-octadecenoyloxy)-22,23-bisnor-5-cholenate, acridine orange 10-dodecyl bromide, acridine orange 10-nonyl bromide, 4-(N,N-dimethyl-N-tetradecylammonium)-methyl-7-hydroxycoumarin) chloride, 5-dodecanoylaminofluorescein, 5-dodecanoylaminofluorescein-bis-4,5-dimethoxy-2-nitrobenzyl ether, 2-dodecylresorufin, fluorescein octadecyl ester, 4-heptadecyl-7-hydroxycoumarin, 5-hexadecanoylaminoeosin, 5-hexadecanoylaminofluorescein, 5-octadecanoylaminofluorescein, N-octadecyl-N'-(5-(fluoresceinyl)) thiourea, octadecyl rhodamine B chloride, 2-(3-(diphenylhexatrienyl)-propanoyl)-1-hexadecanoyl-sn-glycero-3-phosphocholine, 6-N-(7-nitrobenz-2-oxa-1,3-diazol-4-yl)amino)hexanoic acid, 1-hexadecanoyl-2-(1-pyrenedecanoyl)-sn-glycero-3-phosphocholine, 1,1'-dioctadecyl-3,3,3',3'-tetramethyl-indocarbocyanine perchlorate, 12-(9-anthroyloxy)oleic acid, 5-butyl-4,4-difluoro-4-bora-3a,4a-diaza-s-indacene-3-nonanoic acid, N-(lissamine.TM. rhodamine B sulfonyl)-1,2-dihexadecanoyl-sn-glycero-3-phosphoethanolamine, triethylammonium salt, phenylglyoxal monohydrate, naphthalene-2,3-dicarboxaldehyde, 8-bromomethyl-4,4-difluoro-1,3,5,7-tetramethyl-4-bora-3a,4a-diaza-s-indacene, o-phthaldialdehyde, lissamine.TM. rhodamine B sulfonyl chloride, 2',7'-difluorofluorescein, 9-anthronitrile, 1-pyrenesulfonyl chloride, 4-(4-(dihexadecylamino)-styryl)-N-methylpyridinium iodide, chlorins, such as chlorin, chlorine6, bonellin, mono-L-aspartyl chlorine6, mesochlorin, mesotetraphenylisobacteriochlorin, and mesotetraphenylbacteriochlorin, hypocrellin B, purpurins, such as octaethylpurpurin, zinc(II) etiopurpurin, tin(IV) etiopurpurin and tin ethyl etiopurpurin, lutetium texaphyrin, photofrin, metalloporphyrins, protoporphyrin IX, tin protoporphyrin, benzoporphyrin, haematoporphyrin, phthalocyanines, naphthocyanines, merocyanines, lanthanide complexes, silicon phthalocyanine, zinc phthalocyanine, aluminum phthalocyanine, Ge octabutyoxyphthalocyanines, methyl pheophorbide-.alpha.-(hexyl-ether), porphycenes, ketochlorins, sulfonated tetraphenylporphines, .delta.-aminolevulinic acid, texaphyrins, including, for example, 1,2-dinitro-4-hydroxy-5-methoxybenzene, 1,2-dinitro-4-(1-hydroxyhexyl)oxy-5-methoxybenzene, 4-(1-hydroxyhexyl)oxy-5-methoxy-1,2-phenylenediamine, and texaphyrin-metal chelates, including the metals Y(III), Mn(II), Mn(III), Fe(II), Fe(III) and the lanthanide metals Gd(III), Dy(III), Eu(III), La(III), Lu(III) and Tb(III), chlorophyll, carotenoids, flavonoids, bilins, phytochromes, phycobilins, phycoerythrins, phycocyanines, retinoic acids, retinoins, retinates, or combinations of any of the above.

One skilled in the art will readily recognize or can readily determine which of the above compounds are, for example, fluorescent materials and/or photosensitizers. LISSAMINE. is the trademark for N-ethyl-N-[4-[[4-[ethyl[(3-sulfophenyl) methyl]-amino]phenyl](4-sulfophenyl)-methylene]-2,5-cyclohexadien-1-ylidene]3sulfobenzene-methanaminium hydroxide, inner salt, disodium salt and/or ethyl[4-[p[ethyl (m-sulfobenzyl)amino]-.alpha.-(p-sulfophenyl)benzylidene]-2,5cyclohexadien-1-ylidene](m-sulfobenzyl)ammonium hydroxide inner salt disodium salt (commercially available from Molecular Probes, Inc., Eugene, Oreg.). Other suitable photoactive agents for use in the present invention include those described in U.S. Pat. No. 4,935,498, the disclosure of which is hereby incorporated by reference herein in its entirety, such as a dysprosium complex of 4,5,9,24-tetraethyl-16-(1-hydroxyhexyl)oxy-17 methoxypentaazapentacyclo-(20.2.1.1.sup.3,6.1.sup.8, 11.0.sup.14,19)-heptacosa-1,3,5,7,9,11(27),12,14,16,18,20, 22(25),23-tridecaene and dysprosium complex of 2-cyanoethyl-N,N-diisopropyl-6-(4,5,9,24-tetraethyl-17-methoxypentaazapent acyclo-(20.2.1.1.sup.3,6.1.sup.8, 11.0.sup.14,19)-heptacosa-1,3,5,7,9,11(27), 12,14,16,18,20, 22(25),23-tridecaene-16-(1-oxy)hexylphosphoramidite.

In addition, certain ligands, such as, for example, antibodies, peptide fragments, or mimetics of a biologically active ligand may contribute to the inherent therapeutic effects, either as an antagonistic or agonistic, when bound to specific epitopes. As an example, antibody against $\alpha_v\beta_3$ integrin on neovascular endothelial cells has been shown to transiently inhibit growth and metastasis of solid tumors. The efficacy of therapeutic emulsion particles directed to the $\alpha_v\beta_3$ integrin may result from the improved antagonistic action of the targeting ligand in addition to the effect of the therapeutic agents incorporated and delivered by particle itself.

Changes in temperature of the acoustic imaging substance bound to the target can involve increases or decreases in temperature. In embodiments in which the temperature of the acoustic imaging substance is increased, an energy source is used to increase the energy and an increase in acoustic reflectivity is measured.

Local hyperthermia may be induced at the site of targeted nanoparticle emulsions by a variety of modalities including but not limited to ultrasound, shortwave, microwave, magnetic radiation, electromagnetic energies or combination thereof. Such energy may be applied noninvasively by external systems or more invasively by catheter systems. Yang et al. (*Med Biol Eng Comput* 17:518–24, 1979) have shown that microwaves (e.g. 2500 MHz) provide excellent superficial heating to the skin, 900 MHz radiation induces pronounced temperature rises in the musculature and shortwaves at 27 MHz produce a wide plateau of elevated temperature in the muscle layers. These investigators have shown how wave frequency, power, ambient conditions, vasodilation and core boundary conditions can be varied to control local hyperthermia. Others have report the use of ferrimagnetic resonance of a ferrite-impregnated medium as the heating target which is placed internally and heated externally by radiated microwaves. This increased the depth of heating by up to 50% versus nonresonance techniques.

Minimally invasive thermal therapy is a currently used cancer treatment for treating solid tumors and the procedure can also provide the local hyperthemia for temperature-dependent acoustic contrast enhancement of ligand-targeted emulsions. Such approaches impart high temperatures over short time-frames (from microseconds to minutes). Interstitial heating localize the target tissue volume and minimize the effect of heating on surrounding normal tissues. Interstitial heating energy is typically delivered by laser light, microwaves, or ultrasound. The choice of energy source depends on the target site, applicator geometry, and blood perfusion to the site. The decrease of energy with distance due to applicator geometry is more important for targets close to the applicator while the fall-off of energy due to attenuation is more important further from the energy source. Thus, laser light, which is highly scattered in tissues, is appropriately applied to targets close to the applicator and ultrasound or microwaves are better suited for heating deeper structures (Skinner et al., *Phys Med Biol* 43:3535–47, 1998).

The heating effect is believed to is believed to require intensities that are preferably greater than 0.1 W/cm2 (typical ultrasound imaging fields). Also, the prefered intensity level is less than those used for high intensity focused ultrasound (such as, for example, approximately 2000 W/cm2). Additional preferences are that nondestructive pulses and intensity levels be used to leave the tissue itself unharmed. It is believed that high intensity but short pulse durations will also be useful for this application in the range of microseconds to milliseconds, depending on transducer characteristics, depth of tissue interrogated, tissue attenuation, beam dispersion and other physical features. These parameters are themselves distinguishable from more prevalent high intensity focused ultrasound techniques for therapeutic ultrasound uses.

In other instances, the methods of the present invention involve decreasing the temperature of the acoustic imaging substance and measurement of the decrease in reflectivity. The decrease in temperature can be produced by an energy absorbing component such as a cryogenic device for use in cryotherapy. Cryotherapy, which is also sometimes referred to as cryosurgery, is well known in the art involving the use of a liquid nitrogen or liquid argon in a probe as an energy absorber such that the extreme cold kills cancer cells contacted by the probe. (see for example Lee et al., *Urology* 54:135–40, 1999). The methods of the present invention provide an approach for targeting of the energy absorber based upon the decrease in acoustic reflectivity of the acoustic imaging substance bound to the target tissue as well as providing an approach for monitoring the decrease in temperature.

In certain embodiments, the methods of the present invention involve the measurement of the acoustic reflectivity of the acoustic imaging substance upon changing the temperature of the acoustic imaging substance compared to the acoustic reflectivity in absence of the energy source or the energy absorber which changes the temperature of the acoustic imaging substance. The measurement in absence of the energy source or energy absorber can be performed either before or after the energy change. Thus it is possible to measure acoustic reflectivity under control conditions prior to and then immediately after temperature change. Alternatively, the acoustic reflectivity can be measured upon achieving the energy change and then some time later after the energy change has dissipated to return the target to a temperature approaching that prior to the energy change.

The measurement of the difference in acoustic reflectivity can be represented in a number of ways, for example, as a digital numeric representation of the reflectivity difference, as a differential two or three dimensional image, as a colorized differential image and the like.

The present invention also includes devices for performing the methods. The devices measure changes in temperature of a target to which a temperature-sensitive acoustic imaging substance is bound. The device comprises a component configured to change the temperature of the acoustic imaging substance, an ultrasound source configured to transmit acoustic energy to the target, an ultrasound detecting component configured to measure acoustic reflectivity of the surface and a comparator which determines acoustic reflectivity of the target upon changing temperature relative to acoustic reflectivity of the target in absence of changing temperature. The ultrasound transmitting component and ultrasound detecting component are preferably comprised of at least one ultrasound piezoelectric transducer. The temperature changing component can be an energy source, such as a source for ultrasound, shortwave, microwave, magnetic radiation, electromagnetic energy or an energy absorber such as a cryogenic component comprising circulated liquid nitrogen or liquid argon. Preferably, the energy changing component is in the form of a probe.

The comparator component of the device provides the differential measurement in the absence and presence of the temperature change produced by the energy changing component. In one embodiment, the comparator comprises an image processor for producing a differential image based upon a subtraction of the acoustic reflectivity images produced in absence and presence of the energy change. The image processor may include an image frame storage component and/or electronic components such as computer hardware and software components to produce the subtraction image.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the measurement of temperature dependence of ultrasound velocity in perfluorooctane, perfluorodichlorooctane and perfluorooctylbromide.

Ultrasound velocities were determined using a 25 MHz, Panametrics V324 spherically focused transducer. Measurements were made for perfluorooctane, perfluorodichlorooctane or perfluorooctylbromide at discrete temperatures by placing 8 mL of fluorocarbon in a sealed, vertically mounted sample chamber in heated water bath. The back of the chamber consisted of a stainless steel reflector, which extended past the fully enclosed well to allow for water-path and sample-path measurements. The chamber was mounted so that the stainless steel reflector was perpendicular to the insonifying beam.

The times of flight from the transducer to front wall of the chamber and from the transducer to the stainless steel plate were determined for nine independent locations over the sample. The speeds of sound were then averaged together for each temperature. The temperature was changed by two-degree increments from 25 to 47 C by heating the surrounding water bath and allowing time for the sample to reach equilibrium (typically 20 to 25 minutes). Speed of sound was calculated using a previously published algorithm. (Kuo et al., *J. Acoust. Soc. Am.* 88:1679–82, 1990)

Speed of sound measurements are summarized in FIG. 1. As has been previously reported for other liquid perfluorocarbons, the speed of sound showed a linear decrease with increasing temperature for each of the perfluorocarbons.

EXAMPLE 2

This example illustrates the preparation of a biotinylated microemulsion for avidin-biotin targeting.

A biotinylated emulsion was prepared by incorporating biotinylated phosphatidylethanolamine into the outer lipid monolayer of a perfluorocarbon microemulsion. The microemulsion was prepared containing perfluorooctane (40% w/v, 3M), vegetable oil (2% w/v) a surfactant co-mixture (2.0%, w/v) and glycerin (1.7%, w/v) in water as follows. The surfactant co-mixture was prepared by dissolving 64 mole % lecithin (Pharmacia, Inc), 35 mole % cholesterol (Sigma Chemical Co.) and 1 mole % N-(6-(biotinoyl)amino) hexanoyl)-dipalmitoyl-L-alphaphosphatidyl-ethanolamine, Pierce, Inc.) in chloroform. The chloroform-lipid mixture was evaporated under reduced pressure, dried in a 50° C. vacuum oven overnight and dispersed into water by sonication. The suspension was then transferred into a blender cup (Dynamics Corporation of America) with the fluorocarbon, vegetable oil, glycerin and distilled, deionized water and emulsified for 30 to 60 seconds. The emulsified mixture was transferred to a MICROFLUIDICS emulsifier (Microfluidics Co.) and continuously processed at 20,000 PSI for three minutes. The completed emulsion was vialed, blanketed with nitrogen and sealed with stopper crimp seal until use. Particle sizes were determined in triplicate at 37° C. with a laser light scattering submicron particle size analyzer (Malvern Zetasizer 4, Malvern Instruments Ltd, Southborough, Mass.)., which indicated a narrow size distribution with average particle diameter less than 400 nm.

EXAMPLE 3

This example illustrates a method which can be used to prepare an emulsion in which the nanoparticles are conjugated with an F(ab) fragment.

Targeting of emulsions can be achieved by direct chemical conjugation of an antibody to the nanoparticle through a primer material incorporated into the lipid monolayer. The perfluorocarbon nanoparticle contrast agent is prepared as described in Example 1.

F(ab) fragments are generated and isolated using an immunopure F(ab) preparation kit (Pierce, Rockford, Ill.). Briefly, IgG is dialyzed into 20 mM phosphate/10 mM EDTA buffer (pH 7.0), concentrated to 20 mg/ml and digested by immobilized papain. Solubilized F(ab) is purified from Fc fragments and undigested IgG protein using a protein A column. F(ab) fragments are purified from excess cysteine using a G25-150 column and deoxygenated phosphate buffer (pH 6.7). Fraction identity is confirmed by routine SDS-PAGE procedures.

F(ab) fractions are pooled and combined with the primer-derivatized emulsion (1–2 mg F(ab)/ml of emulsion). The mixture is adjusted to pH 6.7, sealed under nitrogen and allowed to react overnight at ambient temperatures with gentle, continuous mixing. The mixture may be subsequently dialyzed with a 300,000 MWCO Spectra/Por DispoDialyzer (Laguna Hills, Calif.) against 10 mM phosphate buffer (pH 7.2) to remove unconjugated F(ab) fragments. The final emulsion is vialed under nitrogen and stored at 4° C. until use. A nonspecific control emulsion may be prepared using the control, irrelevant IgG F(ab) fragments in the above protocol.

EXAMPLE 4

This example illustrates the temperature-dependent targeting of nitrocellulose membranes using microemulsion ultrasound contrast agent bound to the target with avidin-biotin conjugation.

The ultrasonic data acquisition set-up and analysis to measure acoustic reflectance backscatter was as follows. A 25 MHz, spherically focused transducer (0.63 mm diameter, 2.54 mm focal length, Panametrics V324) was mounted on a gantry consisting of three orthogonal sleds. The transducer was translated in a raster scan format by a computer controlled motion controller (Aerotech Unidex 12) with 100 μm resolution. The pulses sent to the motor from the motion controller were counted in a digital counter (National Instruments PCI-1200) and then a trigger was generated for a digital delay generator (Stanford Research Systems DG535). The delay generator then sent a trigger for the pulser (Panametrics 5900) and for the digitizing oscilloscope (Hewlett-Packard 54510B), as well as a delayed trigger for the real time digitizer (Tektronix RTD720A). Traces representing the backscattered ultrasonic wave were captured on the fly as the transducer was scanned over the surface of the clot in a 68×68 (6.8 mm×6.8 mm) grid at 100 μm resolution. The traces were then transferred from the real time digitizer to the controlling computer (Apple Power Macintosh 7300) over GPIB for image reconstruction and data storage. Acquisition typically took about 4 minutes per scan.

The sample chamber consisted of a fully enclosed well with an acoustic aperture to allow insonification of the sample. The chamber was attached through two ports to silicone tubing (Masterflex Platinum, I.D.=⅛") that allowed perfusion of the contrast agent over the sample. A roller pump (Masterflex, Cole-Panner Inc.) was used to drive the flow at a rate of 20 mL/min. The flow system was filled with 20 mL of 50 nM phosphate buffer. The sample chamber and enclosed sample were positioned vertically so that no passive settling of the contrast agent could occur. After initial location of the sample, a bolus of 100 μL of the contrast agent was delivered through an injection port and ultrasonic monitoring was performed initially and after 60 minutes of exposure. The chamber and tubing were then flushed with phosphate buffer.

After confirmation of successful targeting of the contrast agent by imaging, the temperature was varied in 5° C. increments from 27 to 47° C. using an immersion heater controlled by a temperature regulator (DigiSense, Cole-Parmer Inc.). The entire water bath was placed on top of a magnetic stirrer plate to allow for adequate mixing and homogenous temperature distribution throughout the bath. At each temperature point, the focus of the transducer was determined by observing the reflection from a steel plate. The front wall of the sample was then placed at the focus of the transducer.

The reflected ultrasonic signals were full-wave rectified and used to render a peak-detected c-scan image so that a user-defined region of interest could be drawn around the clot or nitrocellulose sample. The signals representing the reflection of the interrogating wave of ultrasound from the surface of the sample were isolated with a rectangular windowing function. The placement of the window was carefully controlled in the case of the thin nitrocellulose samples by an automatic algorithm that placed the end of the window midway between the front and back wall echo of the nitrocellulose paper. The isolated signal was then fast Fourier transformed and the average power over the usable bandwidth (17 to 35 MHz, as determined by 10 dB down points) was calculated in the logarithmic domain. This "integrated power" was then sorted for all of the points in the region of interest and the brightest 100 points were retained for analysis. The integrated power determined at every point in the scan was also used to render images of the change in ultrasonic enhancement of the clot. The frequency-dependent reflection enhancement was averaged for the 100 brightest points and then normalized by subtracting the reflection enhancement for the control scan. This process was performed for each sample.

Nitrocellulose membranes were prepared as follows for avidin-biotin targeting of temperature-dependent targeted emulsions in vitro. Flat nitrocellulose membranes were prepared for contrast binding with a diaminohexane spacer and activated with glutaraldehyde for protein conjugation. Nitrocellulose discs (2.5 cm diameter) were immersed in 1,6 diaminohexane (2.5% w/v, pH 11.9) for 60 minutes under constant rotary agitation. The membranes were next washed under constant agitation for approximately 12 hours in 1M acetic acid followed by 12 hours in ultrapure water with several changes of each medium. The diaminoalkane-modified nitrocellulose membranes were then exposed to 1% glutaraldehyde in 0.5 M $NaHCO_3/Na_2CO_3$, pH 10, for 15 minutes followed by a three hour wash in several changes of ultrapure water. The diaminohexane-modified, glutaraldehyde-activated nitrocellulose membranes were stored dry at 4° C. until use.

Avidin (50 μg) dissolved in 0.1 M phosphate buffered saline (PBS) (pH 7.2–7.4) was spotted and air-dried dropwise onto the center of each membrane with a microliter syringe and allowed to dry. Next, each membrane was washed with three, five-minute changes of PBS-0.1% Tween 20. Dehyrdated milk powder suspended in PBS-0.1% Tween 20 was used to block glutaraldehyde activated protein binding sites left unoccupied after the application of avidin for 20 minutes. Excess protein was removed with three, five minute isotonic, PBS washes.

Five avidin-derivatized and five control nitrocellulose discs were utilized for exposure to biotinylated perfluorooctane particles. After confirmation of successful targeting of the contrast agent by acoustic imaging, the targeted sample temperature was varied in 5° C. increments from 27 to 47° C. using an immersion heater controlled by a temperature regulator (DigiSense, Cole-Parmer Inc.). The entire water bath was placed on top of a magnetic stirrer plate to allow for adequate mixing and homogenous temperature distribution throughout the bath. At each temperature point, the focus of the transducer was determined by observing the reflection from a steel plate. The front wall of the sample was then placed at the focus of the transducer.

Figure 2:
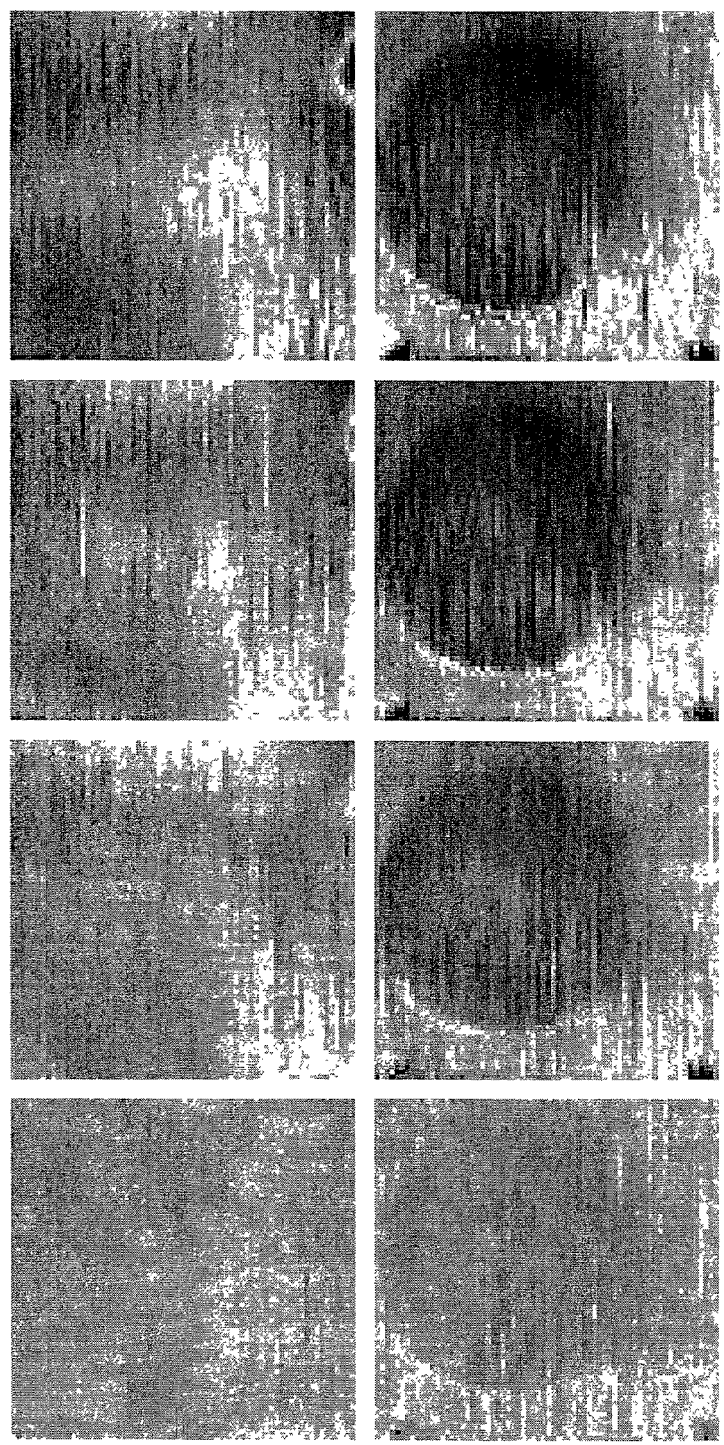
FIG. 2 illustrates the differential ultrasound images obtained from nitrocellulose membranes showing the increase in reflectivity over that measured at 27° C. for temperatures of 32° C., 37° C., 42° C., and 47° C. in which darker grays indicate greater enhancement of reflectivity.
Figure 3:
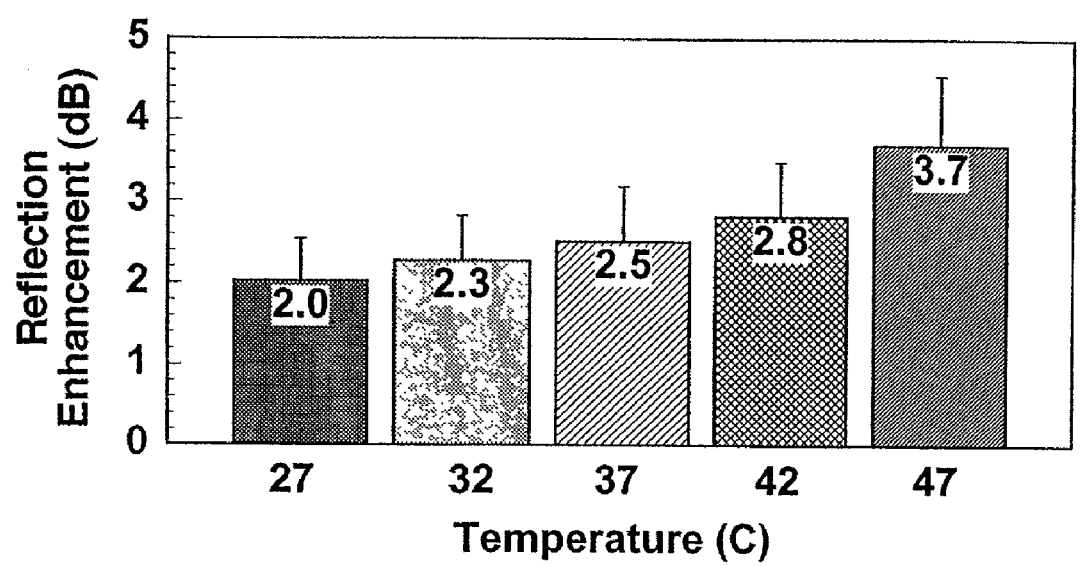
FIG. 3 illustrates the relative change of ultrasonic reflected power as a function of temperature between targeted and control nitrocellulose membranes.
Figure 4:
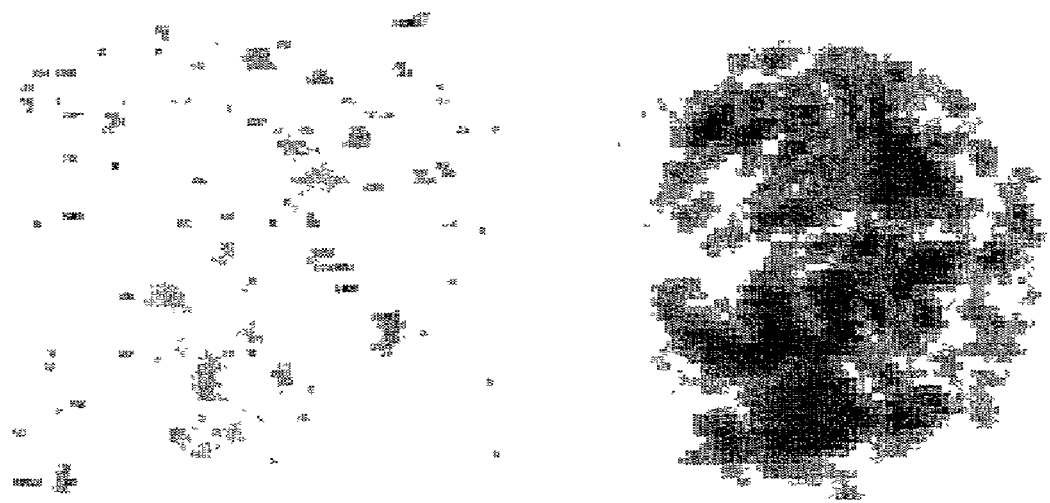
FIG. 4 illustrates the ultrasonic reflection from a human fibrin clot before (left panel) and after (right panel) targeting with contrast agent wherein darker grays represent larger reflection..
Figure 5:
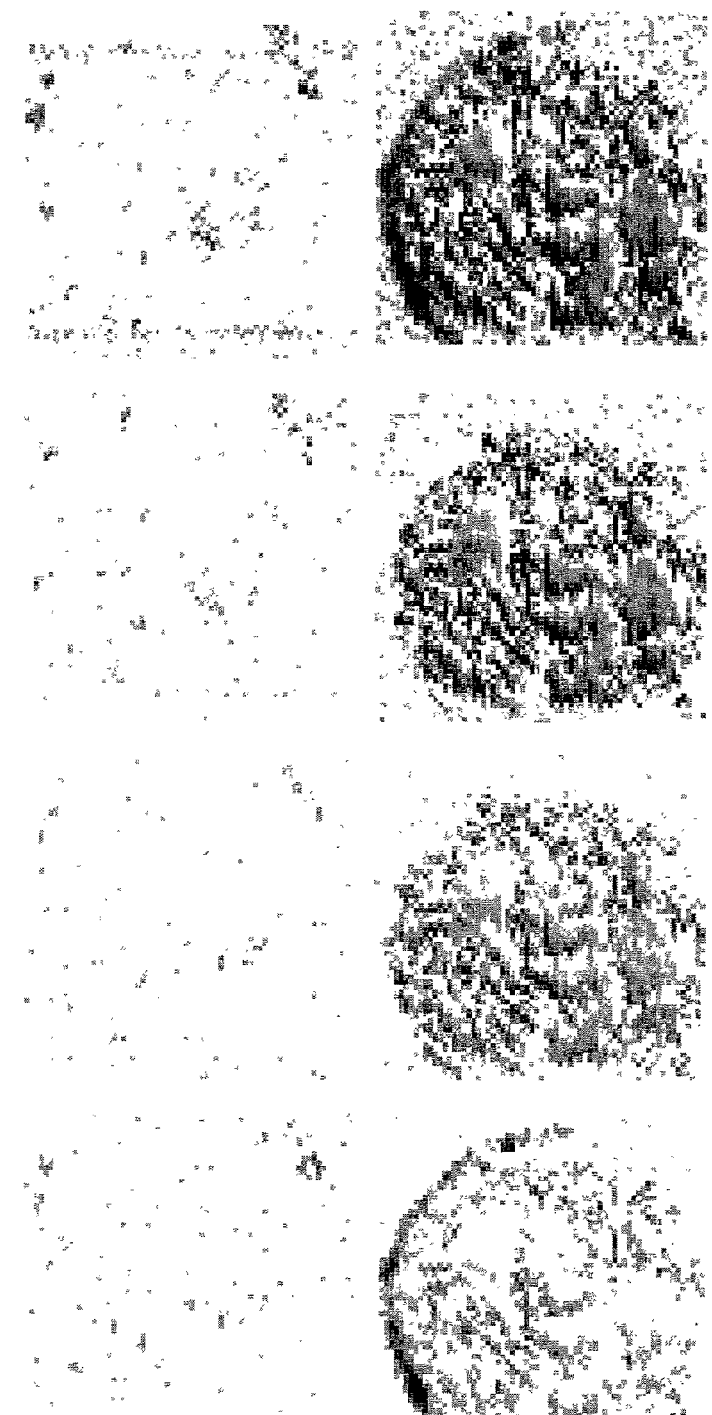
FIG. 5 illustrates the differential ultrasound images obtained from human plasma clots on nitrocellulose membranes showing the increase in reflectivity over that measured at 27° C. for temperatures of 32° C., 37° C., 42° C., and 47° C. in which darker grays indicate greater enhancement of reflectivity.
Figure 6:
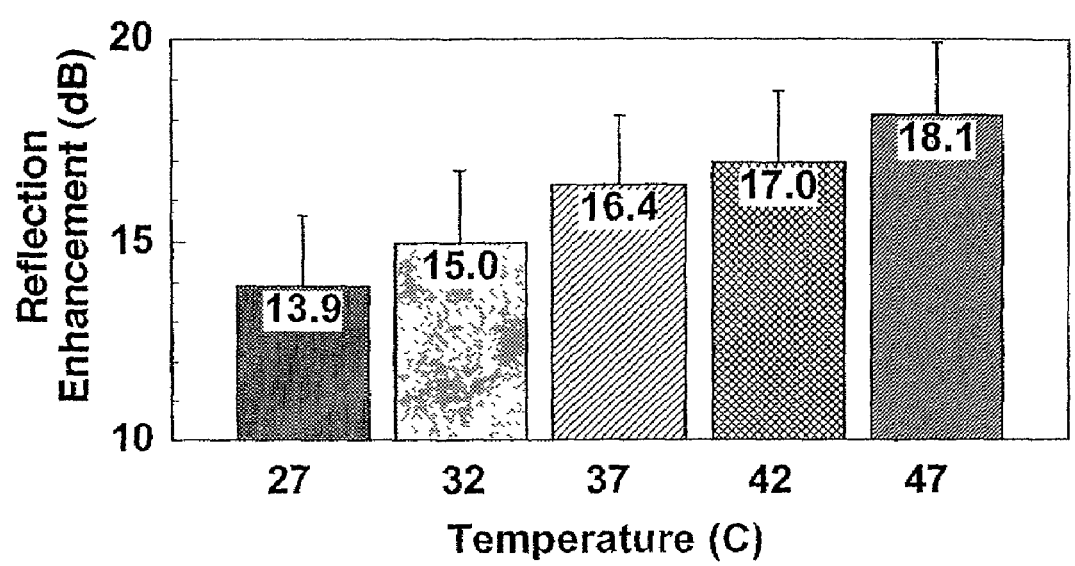
FIG. 6 illustrates the relative change of ultrasonic reflected power as a function of temperature between targeted and control human plasma clots on nitrocellulose membranes.
Figure 7:
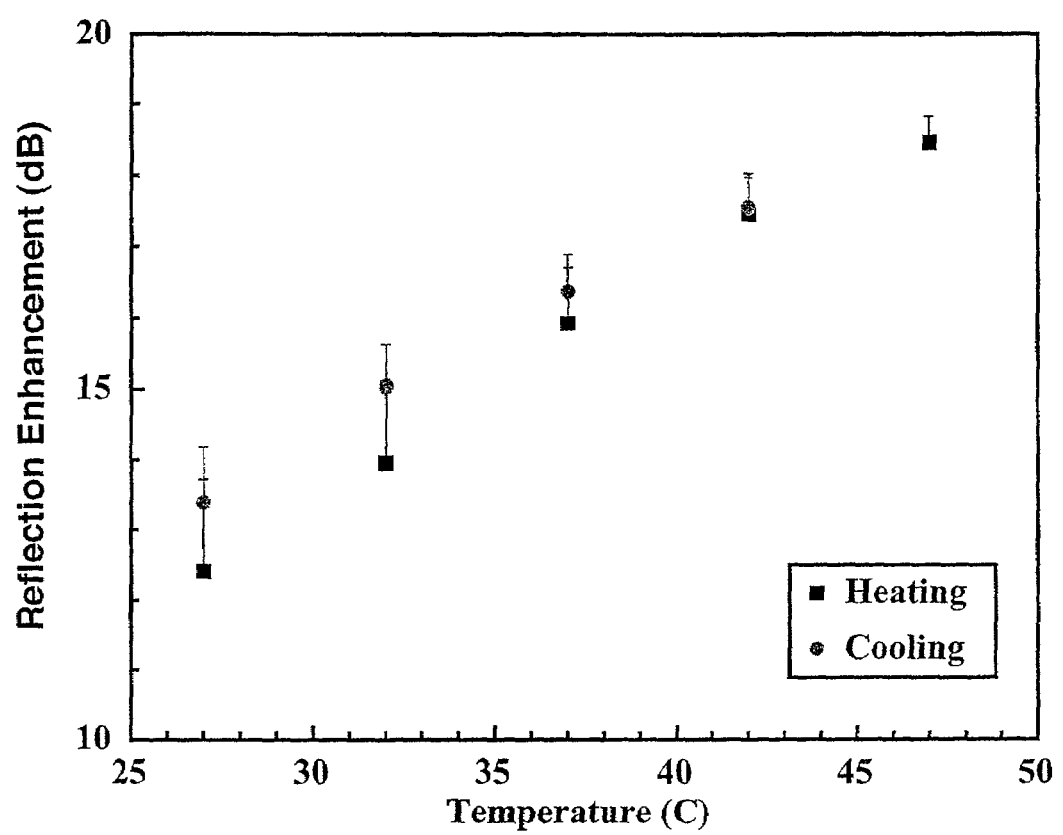
FIG. 7 illustrates the lack of hystersis of the reflection enhancement from human plasma clot plotted as a function of temperature when heated (circles) and then cooled (squares).

FIG. 2 demonstrates the change of ultrasonic reflected power with temperature for targeted and control nitrocellulose membranes. The membranes were spotted with a single drop of avidin resulting in the almost perfectly circular feature. The pictures shows the change in reflected enhancement for the transition from the baseline temperature of 27 C to each individual temperature points. Darker areas represent areas of larger changes in enhancement and can be seen to increase substantially for targeted nitrocellulose in comparison to the control nitrocellulose.

The 100 brightest sites for each nitrocellulose membrane sample were selected to determine the average frequency-dependent reflection enhancement. Each curve was then normalized to the respective reflection enhancement from the control nitrocellulose membrane at the same temperature.

The progressive increase in ultrasonic backscatter enhancement with temperature was further quantified in FIG. 3 with the bandwidth (17 to 34 MHz) limited average. The increased impedance mismatch between the bound nanoparticles and the substrate that occurs with increased temperature results in improved reflection enhancement from targeted substrates. The correlation between contrast enhancement and temperature for nitrocellulose (R=0.95) is excellent. FIGS. 3 quantify the changes in reflection enhancement as a function of temperature. Overall, the increase in enhancement is 0.08 dB/C for nitrocellulose.

EXAMPLE 5

This example illustrates the temperature-dependent targeting of plasma-rich plasma clots on nitrocellulose membranes using microemulsion ultrasound contrast agent bound to the target with avidin-biotin conjugation.

Biotinylated 1H10 Antibody was prepared using the EZ-LINK Sulfo-NHS-LC-Biotinylation Kit. Briefly, 2 to 10 mg of antibody in 1 ml of phosphate buffered saline is combined with Sulfo-NHS-LC-Biotin in distilled water to afford a 12 to 20-fold molar excess of reagent to antibody. The solution was then incubated at room temperature for 30 minutes. Biotinylated antibody was separated from reagents using a 10 ml desalting column. Equilibration and elution was performed with phosphate buffered saline. Fractions of eluate were collected and UV absorbance measured at 280 nm with a spectrophotometer. Fractions containing antibody were stored at 4° C. until use.

Plasma clots were produced on nitrocellulose membrane surfaces by combining human citrated plasma (375 μl) and 100-mM calcium chloride (25 μl) with three units of thrombin in a plastic mold placed on the membranes. The plasma was allowed to coagulate slowly at ambient temperature and then transferred to PBS until exposure to the control or targeted contrast system.

Clots (n=9) were incubated with the biotinylated 1H10 antibody overnight in PBS in a 4° C. cold room under gentle agitation. The clots were then rinsed and exposed to 100 μg of avidin under gentle agitation for one hour at room temperature. The clots were then re-rinsed and ready for exposure to contrast agent as described in Example 4. Control clots (n=7), not pretargeted with biotinylated antibody or avidin, were exposed in identical manner to the biotinylated contrast agent.

Measurement of acoustic reflectivity was performed as in Example 4. The inherently poor echogenicity of the native human plasma clots is shown in the left portion of the FIG. 4. The figure illustrates two images of the integrated reflected power of a plasma clot before and after delivery of the contrast agent, with the grayscale representing a logarithmic depiction of the reflection enhancement. Darker areas on the right picture represent areas where the enhancement of the clot is increased by the presence of site-targeted ultrasonic contrast agent.

The same plasma clot depicted in FIG. 4 is also shown in FIG. 5 where the grayscale now represents the change in enhancement brought about by increases in temperature in 5° C. increments from the 27° C. baseline. As in the case of targeted nitrocellulose, targeted human plasma clots show substantial increase in echogenicity with temperature while the control clots (unexposed to contrast agent) show little change over this temperature range. FIG. 6 shows the results of the reflection enhancement for the 100 brightest sites on the clots averaged over the usable bandwidth of the transducer (17 to 34 MHz). A linear fit to this plot of reflection enhancement vs. temperature yields a correlation coefficient of R=0.99 and a slope of 0.21 dB/C.

In comparison, the control nitrocellulose and control human plasma clots both show only a small change in reflected power as the temperature increases. The targeted or enhanced substrates both exhibit detectable changes in enhancement with as little as a 5° C. change in temperature. This differential acoustic reflectivity response can be utilized to segment between contrast targeted and nontargeted surfaces and enhance image presentations through colorization, digital subtraction or similar techniques. The increased sensitivity of targeted tissue detection as well as capability for improved presentation to and recognition by clinical readers could markedly improve the recognition of pathologies that might have otherwise have been unappreciated.

EXAMPLE 6

This example illustrates the lack of hystersis of temperature-dependent change in acoustic reflectivity of avidin-biotin targeted fluorocarbon emulsion bound to human plasma clot.

To test for the reversibility of the temperature effect, two human plasma clot samples were heated and then cooled and the reflection enhancement recorded for each temperature point using techniques described in example 3. The hysteresis curves are plotted in FIG. 7. Within the error bars of the measurements, the magnitude of enhancement was identical at each temperature, independent of the direction of temperature change. Given the boiling point of the selected fluorocarbon, i.e. perfluorooctane (105° C.), and the heat-dissipating effect of the 37° C. water bath in which the samples were insonified, these results confirm that enhancement or diminishment of acoustic reflectivity of targeted tissues results from temperature-dependent dependent changes in acoustic impedence of the bound emulsion particles and not a phase-transition of the fluorocarbon to a gaseous state.

EXAMPLE 7

This example illustrates methodology and instrumentation that can be used in applying the present invention to ultrasound imaging in conjunction with hyperthermia therapy in specifically detecting, localizing and defining the morphology of the tumor burden and in monitoring the hyperthermia.

Hyperthermia in various forms is now used in conjunction with radiation oncology as an augmentive treatment for various cancers, particularly those less than 8 cm in depth. One device currently used for this application is the Sonotherm® 1000 produced by Labthermics Technologies, Champaign, Ill. Optimal tissue hyperthermia depends on heating the tumor with minimum treatment of surrounding normal tissues. SONOTHERM 1000 has the capability to segment a specified tissue volume into small cubic treatment voxels. By adjusting the frequency and intensity of different elements of the ultrasound array, "optimal" heating patterns are achieved.

The keys to all this regimen, especially with regard to difficult to distinguish small tumors, are (1) the precise localization and morphologic delineation of the tumor in a three-dimensional volume space and (2) noninvasive thermometry of the tissue heating process to ensure tumor kill and sparing of normal collateral tissues.

The temperature-dependent ultrasound contrast agents of the present invention will greatly enhance the high-resolution detection, localization and mapping of tumors in two-dimensional or three-dimensional space, particularly when the cancer is small or the background in inherently acoustically reflective. This is achieved through the differential ultrasonic response of nanoparticle-targeted and surrounding normal tissues. In addition, the temperature-dependent changes in acoustic backscatter could be used an internal thermometry, assuring that targeted tissues are heated to appropriate levels while of other tissue heating is minimized. This high resolution, noninvasive thermometry may be constantly displayed in real-time using a scaled color map to allow the operator to monitor tissue temperatures and manually adjust the hyperthermetry protocol. Alternatively, ultrasonic beam adjustments may be automatically implemented "on-the-fly" by the hyperthermometry machine through self-monitoring algorithms.

Pathologies, such as tumors, are often difficult to differentiate from normal tissues with routine ultrasound and benefit from specific contrast enhancement. Unfortunately, the high acoustic reflectivity of adjacent tissues may often diminish the magnitude of contrast enhancement achieved, even with targeted molecular imaging agents. The opportunity to use temperature dependent, targeted molecular contrast agents further provides a unique mechanism for differentiating normal from pathologic tissues by increasing the acoustic signal from targeted versus normal surrounding tissues. This feature will allow refined segmentation and localization of tumors, particularly small tumors, for biopsy or external radiation or hyperthermic therapy. Improved localization affords more precise focusing of external therapeutic energy sources, maximizing the efficiency of treatment and minimizing colateral damage. In addition, the magnitude of increased acoustic backscatter relative to surrounding tissues provides noninvasive thermometry. The proper level of heating at the target site may be monitored and controlled manually or by self-regulating systems within hyperthermia instrumentation. Technical advantages can be immediately envisioned for the treatment of breast cancer, malignant melanoma, sarcomas, lymphomas, head and neck cancers, and soon more deeply positioned tumors such as colon, cervical, uterine, hepatic, pancreatic, gastric and the like.

For instance, a patient or animal with breast cancer is admitted to the hospital, and an intravenous catheter is placed. Temperature-sensitive acoustic nanoparticles bearing a monoclonal antibody fragment directed against $\alpha_v\beta_3$ integrin on neovascular cells is administered at a dose of between 0.1 and 1.0 ml/kg body weight, preferably 0.25 to 0.5 ml/kg body weight. The agent is allowed to circulate and saturate the neovascular tissue receptors for between 15 minutes and 5 hours, preferably 1 to 2 hours. Baseline ultrasound images are obtained with a standard, commercially available ultrasound imaging device, such as those produced Agilent (Andover, Mass.), Acuson (Mountainview, Calif.), ATL (Bothel, Wash.), GE (Farifield, Conn.) Toshiba (Tokyo, JP), and similar devices. Sonothermography may be instituted with a SONOTHERM 1000 Therapy system (Labthermics Technologies, Champaign, Ill.) or a related device according to the manufactures recommendations for the anticipated location of the suspected mass. The SONOTHERM 1000 is cycled to provide intermittent elevations (lasting less than 10 seconds each) in tissue temperature (between 42.° C. and 45° C.) in the selected region. The differential changes of acoustic contrast of the tumor vasculature targeted with nanoparticles and the surrounding normal tissue are used to specifically detect, localize and define the morphology of the tumor burden. These results are programmed into the SONOTHERM 1000 to refine the location and distribution for the hyperthermic radiation to be imparted. Throughout the subsequent hyperthermia therapy session, the temperature-dependent changes in acoustic backscatter imparted by the targeted nanoparticles within each region of the target tissue may be used to noninvasively determine deep tumor temperature. This information allows fine and continuous regulation of the hyperthermia protocol to closest possible tolerance, minimizing collateral damage to normal tissues and enhancing the overall safety of the procedure

EXAMPLE 8

This example illustrates methodology and instrumentation that can be used in applying the present invention to catheter-directed invasive hyperthermia.

The targeted temperature-dependent nanoparticles can be used in a catheter-based system as follows. A variety of therapeutic ultrasound catheters have been developed that allow highly focused heat generation for therapy and surgical application. An example of such a device is the multi-element array system described by Lee et al. (*IEEE transactions of Biomedical Engineering.* 4:880–90, 1999). This unit has been demonstrated both in vitro and in vivo to achieve a therapeutic temperature rise (above 5° C.) over 92% of a target volume of 30 mm×30 mm×35 mm. This and similar devices provide exquisite control of temperature distribution. This hyperthermia catheter system could be coupled with commercially available, intravascular ultrasound transducer technology to provide both fine detailed ultrasonic imaging of heated tissues at frequencies ranging from 10 to 50 MHz. These dual imaging/therapeutic catheters could be utilized for both endoscopic an intravascular applications.

The catheter for hyperthermia and ultrasound system could be used in treating cancer as in the following example. A patient with suspected pancreatic cancer, would be admitted to the hospital, and an intravenous catheter placed. Temperature-sensitive acoustic nanoparticles bearing a monoclonal antibody fragment directed against $\alpha_v\beta_3$ integrin on neovascular cells is administered at a dose of between 0.1 and 1.0 ml/kg body weight, preferably 0.25 to 0.5 ml/kg. The agent is allowed to circulate and saturate the neovascular tissue receptors for between 15 minutes and 5 hours, preferably 1 to 2 hours. A combinational therapeutic/imaging ultrasonic catheter is advanced and images of the pancreas from a transgastric/transduodenal approach are obtained. The diagnosis, location and extend of the pancreatic tumor is confirmed through a temperature-dependent imaging protocol as previously described. The tumor is insonified to induce localized hyperthermia. The temperature of targeted tissue is monitored continuously by the changes in acoustic backscatter. Incremental temperature differences are color-mapped onto ultrasonic image displays that are repetitively updated and reviewed by the operator. The operator manually or the equipment automatically adjusts intensity or frequency of the ultrasonic beam to optimize tumor destruction and minimize collateral damage to normal tissues.

In view of the above, it will be seen that the several advantages of the invention are achieved and other advantageous results attained.

As various changes could be made in the above methods and compositions without departing from the scope of the invention, it is intended that all matter contained in the above description be interpreted as illustrative and not in a limiting sense.

All references cited in this specification are hereby incorporated by reference. The discussion of the references herein is intended merely to summarize the assertions made by their authors and no admission is made that any reference constitutes prior art. Applicant reserves the right to challenge the accuracy and pertinency of the cited references.

What is claimed is:

1. A method for comparing acoustic reflectivity of a target for ultrasound imaging at a lower and a higher temperature, the method comprising
   (a) measuring reflectivity prior to raising the temperature of liquid nanoparticles bound to a target;
   (b) raising the temperature of the liquid nanoparticles bound to said target sufficiently to produce a measurable enhancement in acoustic reflectivity of the target;
   (c) measuring reflectivity after raising the temperature of the bound liquid nanoparticles; and
   (d) determining the change in reflectivity of the bound liquid nanoparticles after raising the temperature compared to reflectivity prior to raising the temperature,
   wherein said nanoparticles comprise at least one fluorocarbon,
   said nanoparticles having been administered to said target in a non-gaseous emulsion, and wherein said nanoparticles are maintained in the liquid state during all of steps (a)–(c).

2. The method according to claim 1 wherein the fluorocarbon is perfluorooctane.

3. The method according to claim 1 wherein the nanoparticles comprise at least one liquid fluorocarbon encapsulated with at least one lipid surfactant which comprises at least one ligand that binds to said target.

4. The method according to claim 1 wherein the emulsion further comprises a biologically active agent.

5. The method according to claim 1 wherein raising the temperature comprises providing the target with ultrasound or electromagnetic energy or a combination thereof, sufficient to raise the temperature of said nanoparticles, so as to enhance acoustic reflectivity.

6. The method according to claim 1 wherein changing the temperature comprises changing the temperature of the bound nanoparticles by at least 5° C.

7. The method of claim 1 wherein the target resides in a mammalian subject.

8. The method of claim 1 wherein said nanoparticles comprise at least one liquid fluorocarbon encapsulated with at least one lipid surfactant.

9. The method according to claim 3 wherein the ligand is a polypeptide, a peptidomimetic, a polysaccharide, a lipid, or a nucleic acid.

10. The method according to claim 9 wherein the polypeptide is at least a portion of an antibody.

11. The method of claim 7 wherein said subject is human.

12. A method for obtaining an image resulting from enhanced acoustic reflectivity of a target for ultrasound imaging, the method comprising
   (a) changing the temperature of liquid nanoparticles bound to said target sufficiently to produce a measurable enhancement of acoustic reflectivity of the target, and
   (b) obtaining an ultrasound image of said target, bound to said liquid nanoparticles,
   wherein said nanoparticles comprise at least one fluorocarbon, said nanoparticles having been administered to said target in a non-gaseous emulsion; and
   wherein said nanoparticles are maintained in the liquid state during both of steps (a) and (b).

13. The method according to claim 12 wherein the fluorocarbon is perfluorooctane.

14. The method according to claim 12 wherein the nanoparticles comprise at least one perfluorocarbon encapsulated with at least one lipid surfactant which comprises at least one ligand that binds to said target.

15. The method according to claim 12 wherein the emulsion further comprises a biologically active agent.

16. The method according to claim 12 wherein changing the temperature comprises providing the target with ultrasound or electromagnetic energy or a combination thereof, sufficient to raise the temperature of said nanoparticles, so as to enhance acoustic reflectivity.

17. The method according to claim 12 wherein raising the temperature comprises raising the temperature of the bound nanoparticles by at least 5° C.

18. The method of claim 12 wherein the target resides in a mammalian subject.

19. The method of claim 18 wherein said subject is human.

20. The method of claim 12 wherein said nanoparticles comprise at least one liquid fluorocarbon encapsulated with at least one lipid surfactant.

21. The method according to claim 14 wherein the ligand is a polypeptide, a peptidomimetic, a polysaccharide, a lipid, or a nucleic acid.

22. The method according to claim 21 wherein the polypeptide is at least a portion of an antibody.

* * * * *